United States Patent
Stemmer et al.

(10) Patent No.: US 6,489,146 B2
(45) Date of Patent: Dec. 3, 2002

(54) END-COMPLEMENTARY POLYMERASE REACTION

(75) Inventors: Willem P.C. Stemmer, Los Gatos; Robert J. Lipshutz, Palo Alto, both of CA (US)

(73) Assignees: Glaxo Group Limited, Middlesex (GB); Affymatrix, Inc., Santa Clara, CA (US)

( * ) Notice: Subject to any disclaimer, the term of this patent is extended or adjusted under 35 U.S.C. 154(b) by 0 days.

(21) Appl. No.: 09/245,802

(22) Filed: Feb. 5, 1999

(65) Prior Publication Data

US 2001/0049125 A1 Dec. 6, 2001

Related U.S. Application Data

(63) Continuation of application No. 08/675,502, filed on Jul. 3, 1996, now Pat. No. 5,928,905, which is a continuation of application No. PCT/US96/05480, filed on Apr. 18, 1996, which is a continuation-in-part of application No. 08/425,684, filed on Apr. 18, 1995, now Pat. No. 5,834,252.

(51) Int. Cl.[7] .............................. C12P 19/34; C12Q 1/68
(52) U.S. Cl. .......................... 435/91.1; 435/91.2; 435/6
(58) Field of Search ..................................... 435/91.2, 6

(56) References Cited

U.S. PATENT DOCUMENTS

| | | | |
|---|---|---|---|
| 4,458,066 A | 7/1984 | Caruthers et al. ............. 336/27 |
| 4,683,195 A | 7/1987 | Mullis et al. ................... 435/6 |
| 4,683,202 A | 7/1987 | Mullis .......................... 435/91 |
| 4,800,159 A | 1/1989 | Mullis et al. ............. 435/172.3 |
| 4,965,188 A | * 10/1990 | Mullis et al. ................... 435/6 |
| 5,023,171 A | 6/1991 | Ho et al. |
| 5,066,584 A | 11/1991 | Gyllensten et al. ........... 435/91 |
| 5,118,604 A | 6/1992 | Weissman et al. ............. 435/6 |
| 5,279,952 A | 1/1994 | Wu .......................... 435/172.3 |
| 5,286,632 A | 2/1994 | Jones ........................ 435/91.2 |
| 5,340,728 A | 8/1994 | Grosz et al. ................ 435/91.2 |
| 5,582,989 A | * 12/1996 | Caskey et al. .................. 435/6 |
| 5,756,316 A | 5/1998 | Schellenberger ........... 435/91.2 |

FOREIGN PATENT DOCUMENTS

| | | | |
|---|---|---|---|
| WO | WO 96/05296 | 2/1996 | ........... C12N/15/10 |

OTHER PUBLICATIONS

Prodromou et al. Recursive PCR: a novel technique for total gene synthesis, Protein Engineering, 1992, vol. 5(8), p. 827–829.*

Horton et al., "Engineering Hybrid Genes Without the Use of Restriction Enzymes: Gene Splicing by Overlap Extension", *Gene*, 77:61–68 (1989).

Jones et al., "A Rapid Method for Site–Specific Mutagenesis and Directional Subcloning by Using the Polymerase Chain Reaction to Generate Recombinant Circles", *Biotechniques*, 8(2):178–183 (1990).

Oliner et al., "In Vivo Cloning of PCR Products in *E. Coli*", *Nucl. Acids Res.*, 21(22):5192–5197 (1993).

Silver et al., "Novel Use of Polymerase Chain Reaction to Amplify Cellular DNA Adjacent to an Integrated provirus", *J. Virol.*, 63(5):1924–1928 (1989).

(List continued on next page.)

*Primary Examiner*—Gary Benzion
*Assistant Examiner*—Joyce Tung
(74) *Attorney, Agent, or Firm*—Townsend and Townsend and Crew LLP

(57) ABSTRACT

The present invention is directed to a process for amplifying and detecting any target nucleic acid sequence contained in a nucleic acid or mixture thereof and for assembling large polynucleotides from component polynucleotides, each involving generating concatemers formed by PCR amplification of overlapping fragments.

8 Claims, 24 Drawing Sheets

OTHER PUBLICATIONS

Stemmer, "Rapid Evolution of a Protein In Vitro by DNA Shuffling", *Nature*, 370:389–391 (1994).

Suzuki et al., "In Vivo Ligation of Linear DNA Molecules to Circular Forms in the Yeast *Saccharomyces cerevisiae*", *Bacteriology*,155(2):747–754 (1983).

Triglia et al., "A Procedure for In Vitro Amplification of DNA Segments That Lie Outside the Boundaries of Known Sequences", *Nucl. Acids Res.*, 16(16):8186 (1988).

Vallette et al., "Construction of Mutant and Chimeric Genes Using the Polymerase Chain Reaction", *Nucl. Acids Res.*, 17(2):723–733 (1989).

White et al., "Concatemer Chain Reaction: a Taq DNA Polymerase–Mediated Mechanism for Generating Long Tandemly Repetitive DNA Sequences", *Anal. Biochem.*, 199:184–190 (1991).

* cited by examiner

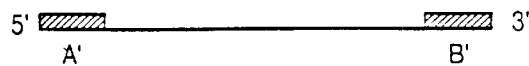
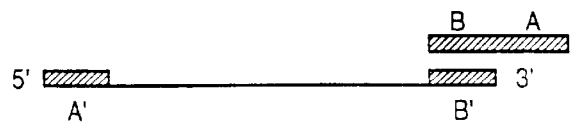
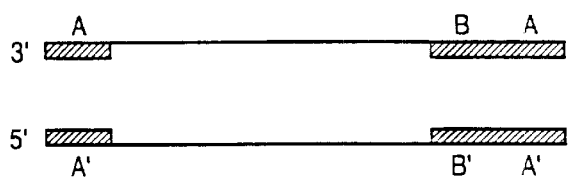
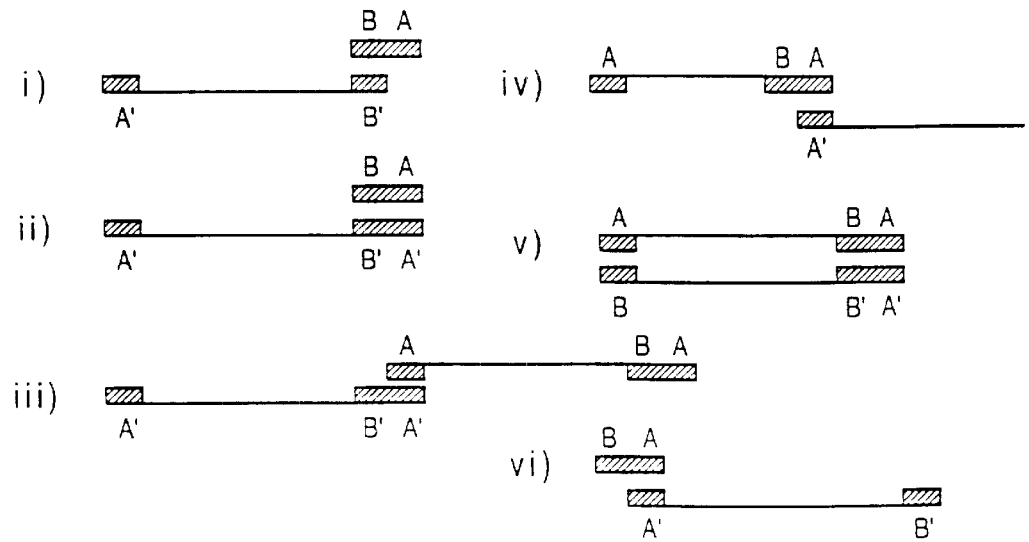
FIG. 1A

④ EXTEND
ONLY HYBRIDS i, ii, iii EXTEND
⑤ MELT
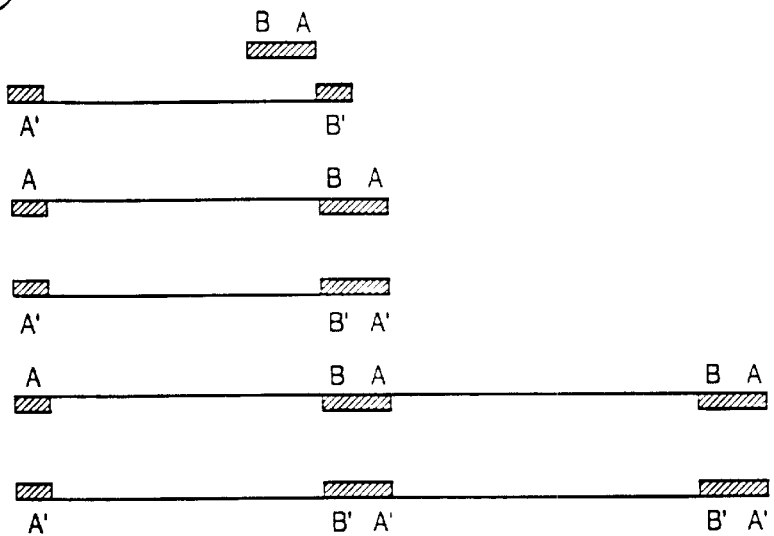
REANNEALING GIVES THE FOLLOWING POSSIBLE
EXTENDIBLE HYBRIDS
    i, ii, iii FROM STEP 4
AND
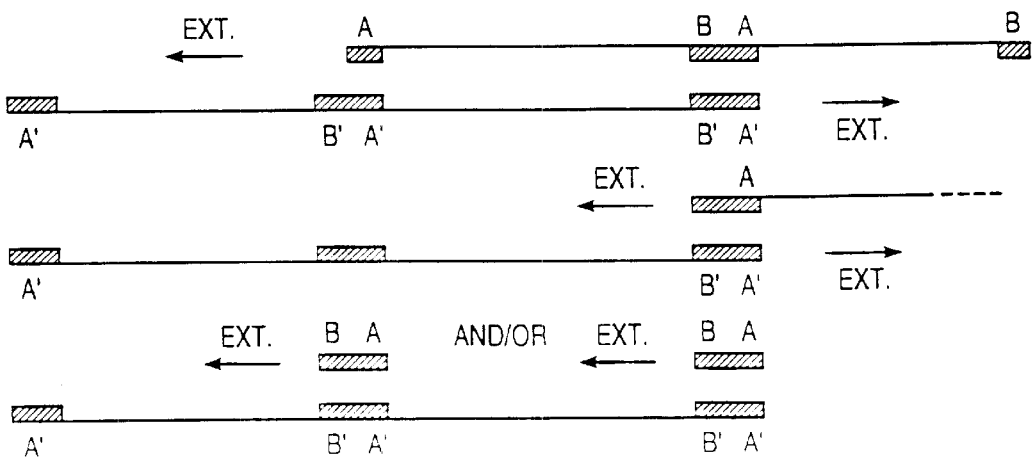
FIG. 1B

| | | | | | | | | | | | | |
|---|---|---|---|---|---|---|---|---|---|---|---|---|
| R1  | CTC | ACG | TTA | AGG | GAT | TTT | GGT | CAT | GAG | ATT | ATC | AAA | AAG | G |
| R2  | ATC | TTC | ACC | TAG | ATC | CTT | TTA | AAT | TAA | AAA | TGA | AGT | TTT | A |
| R3  | AAT | CAA | TCT | AAA | GTA | TAT | ATG | AGG | CCT | GAC | AGG | CCG | GTC | T |
| R4  | GAC | AGT | TAC | CAA | TGC | TTA | ATC | AGT | GAG | GCA | CCT | ATC | TCA | G |
| R5  | CGA | TCT | GTC | TAT | TTC | GTT | CAT | CCA | TGG | TTG | CCT | GAC | TCC | C |
| R6  | CGT | CGT | GTA | GAT | AAC | TAC | GAT | ACG | GGA | GGG | CTT | ACC | ATC | T |
| R7  | GGC | CCC | AGT | GCT | GCA | ATG | ATA | CCG | CGA | GAC | CCA | CGC | TCA | C |
| R8  | CGG | CTC | CAG | ATT | TAT | CAG | CAA | TAA | ACC | AGC | CAG | CTG | GAA | G |
| R9  | GGC | CGA | GCG | CAG | AAG | TGG | TCC | TGC | AAC | TTT | ATC | CGC | CTC | C |
| R10 | ATC | CAG | TCT | ATT | AAT | TGT | TGC | CGG | GAA | GCT | AGA | GTA | AGT | A |
| R11 | GTT | CGC | CAG | TTA | ATA | GTT | TGC | GCA | ACG | TTG | TTG | CCA | TGG | C |
| R12 | TAC | AGG | CAT | CGT | GGT | GTC | ACG | CTC | GTC | GTT | TGG | AAT | GGC | T |
| R13 | TCA | TTC | AGC | TCC | GGT | TCC | CAA | CGA | TCA | AGG | CGA | GTT | ACA | T |
| R14 | GAT | CCC | CCA | TGT | TGT | GCA | AAA | AAG | CGG | TTA | GCT | CCT | TCG | G |
| R15 | TCC | TCC | GAT | CGT | TGT | CAG | AAG | TAA | GTT | GGC | TGC | AGT | GTT | A |
| R16 | TCA | CTC | ATG | GTT | ATG | GCA | GCA | CTG | CAT | AAT | TCT | CTT | ACT | G |
| R17 | TCA | TGC | CAT | CCG | TAA | GAT | GCT | TTT | CTG | TGA | CTG | GTG | AGT | A |
| R18 | CTC | AAC | CAA | GTC | ATT | CTG | AGA | ATA | GTG | TAT | GCG | GCG | ACC | G |
| R19 | AGT | TGC | TCT | TGC | CCG | GCG | TCA | ATA | CGG | GAT | AAT | ACC | GCG | C |
| R20 | CAC | ATA | GCA | GAA | CTT | TAA | AAG | TGC | TCA | TCA | TTG | GAA | AAC | G |
| R21 | TCC | TTC | GGG | GCG | AAA | ACT | CTC | AAG | GAT | CTT | ACC | GCT | GTT | G |
| R22 | AGA | TCC | AGT | TCG | ATG | TAA | CCC | ACT | CGT | GCA | CCC | AAC | TGA | T |
| R23 | CTT | CAG | CAT | CTT | TTA | CTT | TCA | CCA | GCG | TTT | CTG | GGT | GAG | C |
| R24 | AAA | AAC | AGG | AAG | GCA | AAA | TGC | CGC | AAA | AAA | GGG | AAT | AAG | G |
| R25 | GCG | ACA | CGG | AAA | TGT | TGA | ATA | CTC | ATA | CTC | TTC | CTT | TTT | C |
| R26 | AAT | ATT | ATT | GAA | GCA | TTT | ATC | AGT | GTT | ATT | GTC | TCA | TGA | G |
| R27 | CGG | ATA | CAT | ATT | TGA | ATG | TAT | TTA | GGC | CAT | GGT | GGC | CAA | A |
| R28 | AAT | AAA | CAA | ATA | GGG | GTT | CCG | CGC | ACA | TTT | CCC | CGA | AAA | G |

FIG. 5A

| | | | | | | | | | | | | |
|---|---|---|---|---|---|---|---|---|---|---|---|---|
| 1 | TTC | TTA | GAC | GTC | AGG | TGG | CAC | TTT | TCG | GGG | AAA | TGT | GCG | C |
| 2 | GGA | ACC | CCT | ATT | TGT | TTA | TTT | TTG | GCC | ACC | ATG | GCC | TAA | A |
| 3 | TAC | ATT | CAA | ATA | TGT | ATC | CGC | TCA | TGA | GAC | AAT | AAC | CCT | G |
| 4 | ATA | AAT | GCT | TCA | ATA | ATA | TTG | AAA | AAG | GAA | GAG | TAT | GAG | T |
| 5 | ATT | CAA | CAT | TTC | CGT | GTC | GCC | CTT | ATT | CCC | TTT | TTT | GCG | G |
| 6 | CAT | TTT | GCC | TTC | CTG | TTT | TTG | CTC | ACC | CAG | AAA | CGC | TGG | T |
| 7 | GAA | AGT | AAA | AGA | TGC | TGA | AGA | TCA | GTT | GGG | TGC | ACG | AGT | G |
| 8 | GGT | TAC | ATC | GAA | CTG | GAT | CTC | AAC | AGC | GGT | AAG | ATC | CTT | G |
| 9 | AGA | GTT | TTC | GCC | CCG | AAG | AAC | GTT | TTC | CAA | TGA | TGA | GCA | C |
| 10 | TTT | TAA | AGT | TCT | GCT | ATG | TGG | CGC | GGT | ATT | ATC | CCG | TAT | T |
| 11 | GAC | GCC | GGG | CAA | GAG | CAA | CTC | GGT | CGC | CGC | ATA | CAC | TAT | T |
| 12 | CTC | AGA | ATG | ACT | TGG | TTG | AGT | ACT | CAC | CAG | TCA | CAG | AAA | A |
| 13 | GCA | TCT | TAC | GGA | TGG | CAT | GAC | AGT | AAG | AGA | ATT | ATG | CAG | T |
| 14 | GCT | GCC | ATA | ACC | ATG | AGT | GAT | AAC | ACT | GCA | GCC | AAC | TTA | C |
| 15 | TTC | TGA | CAA | CGA | TCG | GAG | GAC | CGA | AGG | AGC | TAA | CCG | CTT | T |
| 16 | TTT | GCA | CAA | CAT | GGG | GGA | TCA | TGT | AAC | TCG | CCT | TGA | TCG | T |
| 17 | TGG | GAA | CCG | GAG | CTG | AAT | GAA | GCC | ATT | CCA | AAC | GAC | GAG | C |
| 18 | GTG | ACA | CCA | CGA | TGC | CTG | TAG | CCA | TGG | CAA | CAA | CGT | TGC | G |
| 19 | CAA | ACT | ATT | AAC | TGG | CGA | ACT | ACT | TAC | TCT | AGC | TTC | CCG | G |
| 20 | CAA | CAA | TTA | ATA | GAC | TGG | ATG | GAG | GCG | GAT | AAA | GTT | GCA | G |
| 21 | GAC | CAC | TTC | TGC | GCT | CGG | CCC | TTC | CAG | CTG | GCT | GGT | TTA | T |
| 22 | TGC | TGA | TAA | ATC | TGG | AGC | CGG | TGA | GCG | TGG | GTC | TCG | CGG | T |
| 23 | ATC | ATT | GCA | GCA | CTG | GGG | CCA | GAT | GGT | AAG | CCC | TCC | CGT | A |
| 24 | TCG | TAG | TTA | TCT | ACA | CGA | CGG | GGA | GTC | AGG | CAA | CCA | TGG | A |
| 25 | TGA | ACG | AAA | TAG | ACA | GAT | CGC | TGA | GAT | AGG | TGC | CTC | ACT | G |
| 26 | ATT | AAG | CAT | TGG | TAA | CTG | TCA | GAC | CGG | CCT | GTC | AGG | CCT | C |
| 27 | ATA | TAT | ACT | TTA | GAT | TGA | TTT | AAA | ACT | TCA | TTT | TTA | ATT | T |
| 28 | AAA | AGG | ATC | TAG | GTG | AAG | ATC | CTT | TTT | GAT | AAT | CTC | ATG | A |

FIG. 5B

{58F}
GGAAAACCCTGGCGTTACCCAACTTAATCGCCTTGCAGCA
{59F}
CATCCCCCTTTCGCCAGCTGGCGTAATAGCGAAGAGGCCC
{60F}
GCACCGATCGCCCTTCCCAACAGTTGCGTAGCCTGAATGG
{61F}
CGAATGGCGCCTGATGCGGTATTTTCTCCTTACGCATCTG
{62F}
TGCGGTATTTCACACCGCATATGGTGCACTCTCAGTACAA
{63F}
TCTGCTCTGATGCCGCATAGTTAAGCCAGCCCCGACACCC
{64F}
GCCAACACCCGCTGACGCGCCCTGACGGGCTTGTCTGCTC
{65F}
CCGGCATCCGCTTACAGACAAGCTGTGACCGTCTCCGGGA
{66F}
GCTGCATGTGTCAGAGGTTTTCACCGTCATCACCGAAACG
{30R}
CGAGGCCCTTTCGTCTCGCGCGTTTCGGTGATGACGGTGA
{31R}
AAACCTCTGACACATGCAGCTCCGGAGACGGTCACAGCT
{32R}
TGTCTGAAGCGGATGCCGGGAGCAGACAAGCCCGTCAGG
{33R}
GCGCGTCAGCGGGTGTTGGCGGGTGTCGGGGCTGGCTTAA
{34R}
CTATGCGGCATCAGAGCAGATTGTACTGAGAGTGCACCAT
{35R}
ATGCGGTGTGAAATACCGCCAGATGCGTAAGGAGAAAAT
{36R}
ACCGCATCAGGCGCCATTCGCCATTCAGGCTACGCAACTG
{37R}
TTGGGAAGGGCGATCGGTGCGGGCCTCTTCGCTATTACGC
{38R}
CAGCTGGCGAAAGGGGGATGTGCTGCAAGGCGATTAAGTT
{39R}
GGGTAACGCCAGGGTTTTCCCAGTCACGACGTTGTAAAAC
{40R}
GACGGCCAGTGCCAAGCTTGCATGCCTGCAGGTCGACTCT
{41R}
AGAGGATCCCCGGGTACCGGAGCTCGAATTCGTAATCATGG
{42R}
TCATAGCTGTTTCCTGTGTGAAATTGTTATCCGCTACAA
{43R}
TTCCACACAACATACGAGCCGGAAGCATAAAGTGTAAAGC
{44R}
CTGGGGTGCCTAATGAGTGAGCTAACTCACATTAATTGCG

FIG. 5C

{45R}
TTGCGCTCACTGCCCGCTTTCCAGTCGGGAAACCTGTCGT
{46R}
GCCAGCTGCATTAATGAATCGGCCAACGCGCGGGGAGAGG
{47R}
CGGTTTGCGTATTGGGCGCTCTTCCGCTTCCTCGCTCACT
{48R}
GACTCGCTGCGCTCGGTCGTTCGGCTGCGGCGAGCGGTAT
{48R}
GACTCGCTGCGCTCGGTCGTTCGGCTGCGGCGAGCGGTAT
{49R}
CAGCTCACTCAAAGGCGGTAATACGGTTATCCACAGAATC
{50R}
AGGGGATAACGCAGGAAAGAACATGTGAGCAAAAGGCCAG
{51R}
CAAAAGGCCAGGAACCGTAAAAAGGCCGCGTTGCTGGCGT
{52R}
TTTTCCATAGGCTCCGCCCCCCTGACGAGCATCACAAAAA
{53R}
TCGACGCTCAAGTCAGAGGTGGCGAAACCCGACAGGACTA
{54R}
TAAAGATACCAGGCGTTTCCCCCTGGAAGCTCCCTCGTGC
{55R}
GCTCTCCTGTTCCGACCCTGCCGCTTACCGGATACCTGTC
{56R}
CGCCTTTCTCCCTTCGGGAAGCGTGGCGCTTTCTCAATGC
{57R}
TCACGCTGTAGGTATCTCAGTTCGGTGTAGGTCGTTCGCT
{58R}
CCAAGCTGGGCTGTGTGCACGAACCCCCCGTTCAGCCCGA
{59R}
CCGCTGCGCCTTATCCGGTAACTATCGTCTTGAGTCCAAC
{60R}
CCGGTAAGACACGACTTATCGCCACTGGCAGCAGCCACTG
{61R}
GTAACAGGATTAGCAGAGCGAGGTATGTAGGCGGTGCTAC
{62R}
AGAGTTCTTGAAGTGGTGGCCTAACTACGGCTACACTAGA
{63R}
AGAACAGTATTTGGTATCTGCGCTCTGCTGAAGCCAGTTA
{64R}
CCTTCGGAAAAAGAGTTGGTAGCTCTTGATCCGGCAAACA
{65R}
AACCACCGCTGGTAGCGGTGGTTTTTTTGTTTGCAAGCAG
{66R}
AACCACCGCTGGTAGCGGTGGTTTTTTTGTTTGCAAGCAG
{67R}
TGATCTTTTCTACGGGGTCTGACGCTCAGTGGAACGAAAA

{67F}
CGCGAGACGAAAGGGCCTCGTGATACGCCTATTTTTATAGGTAATGTCATGATAA

{29R}
TGCCACCTGACGTCTAAGAAACCATTATTATCATGACATTAACCTAT

FIG. 5D

{29F}
CCAAAATCCCTTAACGTGAGTTTTCGTTCCACTGAGCGTC
{30F}
AGACCCGTAGAAAAGATCAAAGGATCTTCTTGAGATCCT
{31F}
TTTTTTCTGCGCGTAATCTGCTGCTTGCAAACAAAAAAAC
{32F}
CACCGCTACCAGCGGTGGTTTGTTTGCCGGATCAAGAGCT
{33F}
ACCAACTCTTTTTCGAAGGTAACTGGCTTCAGCAGAGCG
{34F}
CAGATACCAAATACTGTCCTTCTAGTGTAGCCGTAGTTAG
{35F}
GCCACCACTTCAAGAACTCTGTAGCACCGCCTACATACCT
{36F}
CGCTCTGCTAATCCTGTTACCAGTGGCTGCTGCCAGTGGC
{37F}
GATAAGTCGTGTTTACCGGGTTGGACTCAAGACGATAGT
{38F}
TACCGGATAAGGCGCAGCGGTCGGGCTGAACGGGGGGTTC
{39F}
GTGCACACAGCCCAGCTTGGAGCGAACGACCTACACCGAA
{40F}
CTGAGATACCTACAGCGTGAGCATTGAGAAAGCGCCACGC
{41F}
TTCCCGAAGGGAGAAAGGCGGACAGGTATCCGGTAAGCGG
{42F}
CAGGGTCGGAACAGGAGAGCGCACGAGGGAGCTTCCAGGG
{43F}
GGAAACGCCTGGTATCTTTATAGTCCTGTCGGGTTTCGCC
{44F}
ACCTCTGACTTGAGCGTCGATTTTTGTGAGCTCGTCAGG
{45F}
GGGGCGGAGCCTATGGAAAAACGCCAGCAACGCGGCCTTT
{46F}
TTAACGGTTCCTGGCCTTTTGCTGGCCTTTTGCTCACATGT
{47F}
TCTTTCCTGCGTTATCCCCTGATTCTGTGGATAACCGTAT
{48F}
TACCGCCTTTGAGTGAGCTGATACCGCTCGCCGCAGCCGA
{49F}
ACGACCGAGCGCAGCGAGTCAGTGACGAGGAAGCGGAAG
{50F}
AGCGCCCAATACGCAAACCGCCTCTCCCCGCGCGTTGGCC
{51F}
GATTCATTAATGCAGCTGGCACGACAGGTTTCCCGACTGG
{52F}
AAAGCGGGCAGTGAGCGCAACGCAATTAATGTGAGTTAGC
{53F}
TCACTCATTAGGCACCCCAGGCTTTACACTTTATGCTTCC
{54F}
GGCTCGTATGTTGTGTGGAATTGTGAGCGGATAACAATTT
{55F}
CACACAGGAAACAGCTATGACCATGATTACGAATTCGAGC
{56F}
TCGGTACCCGGGGATCCTCTAGAGTCGACCTGCAGGCATG
{57F}
CAAGCTTGGCACTGGCCGTCGTTTTACAACGTCGTGACTG

FIG. 5E

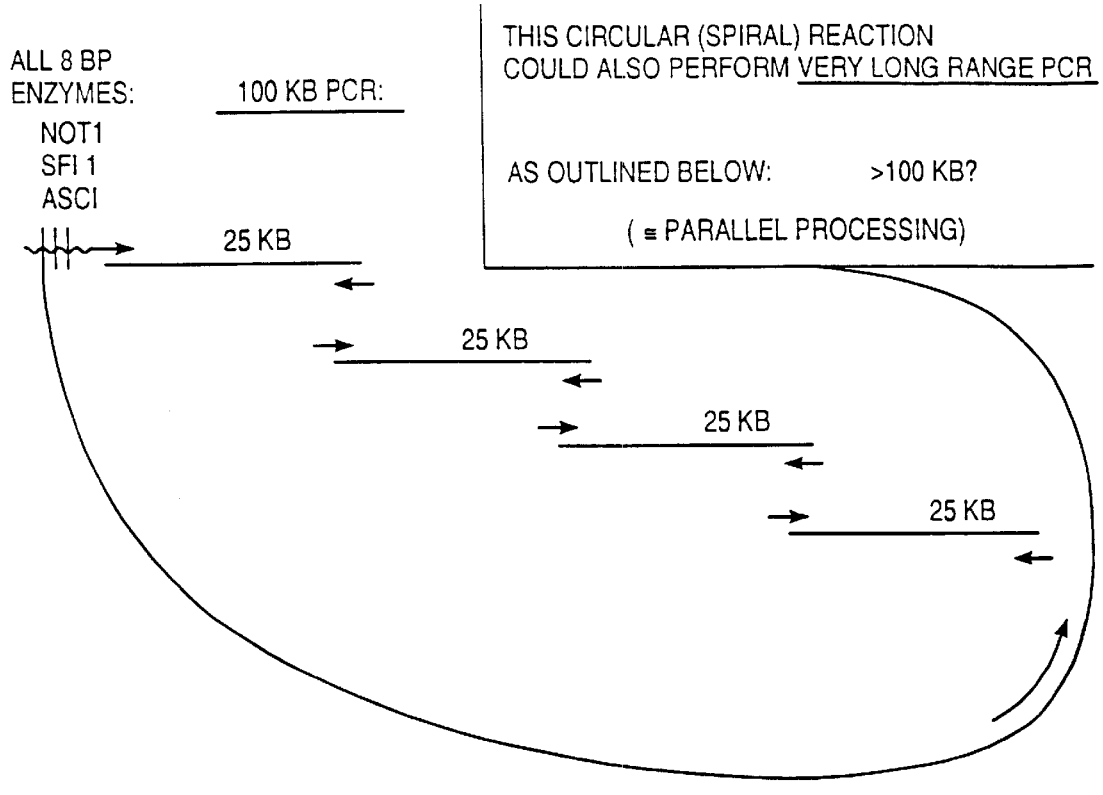
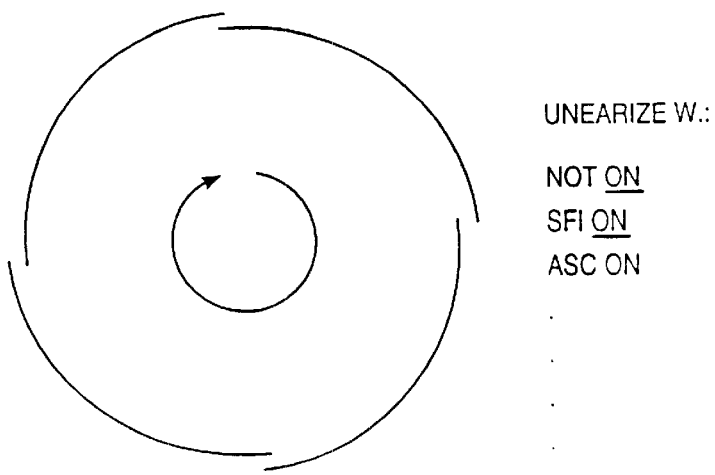
FIG. 8

CONTINUOUS CIRCULAR MULTIPLEX PCR
INITIAL CONDITIONS
ANNEAL WITH PRIMERS
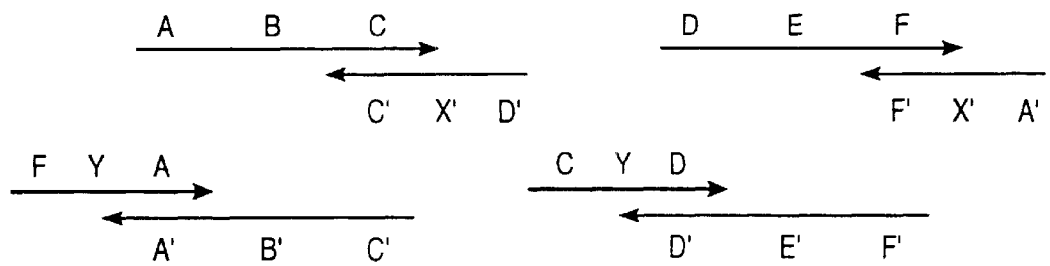
EXTEND AND MELT
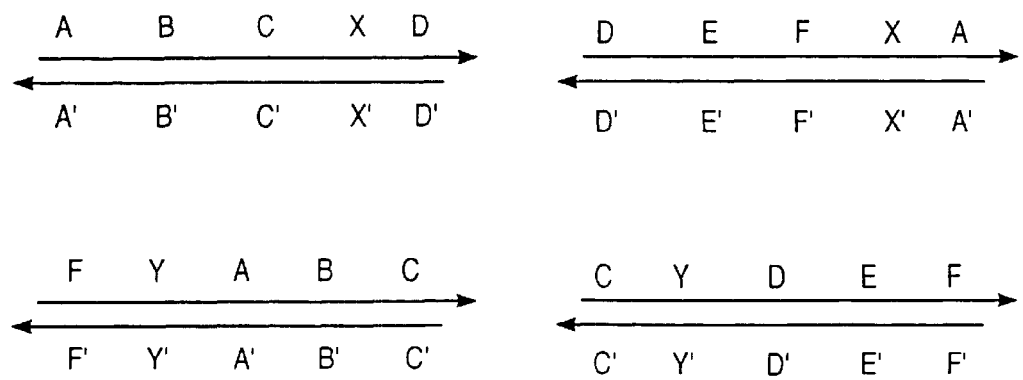
FIG. 9A

REANNEAL
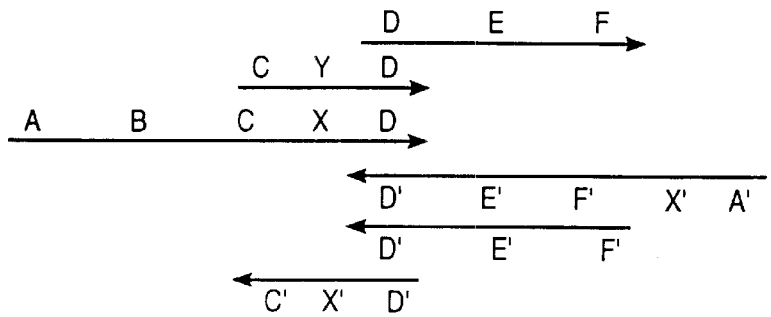
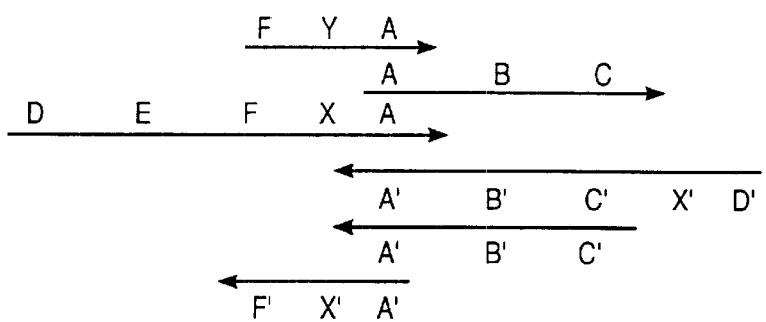
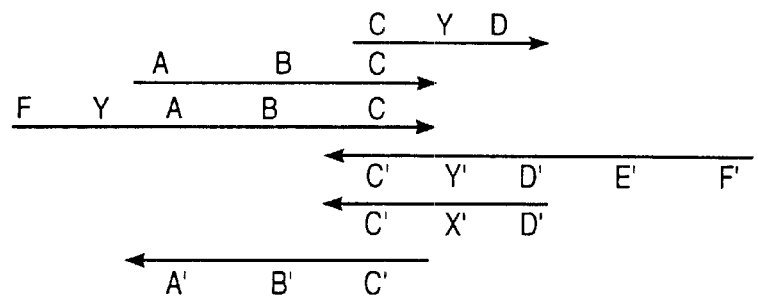
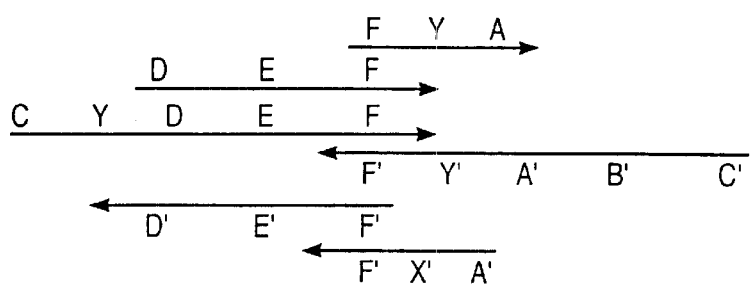
FIG. 9B

CONTINUOUS LINEAR MULTIPLEX PCR
INITIAL CONDITIONS
ANNEAL WITH PRIMERS
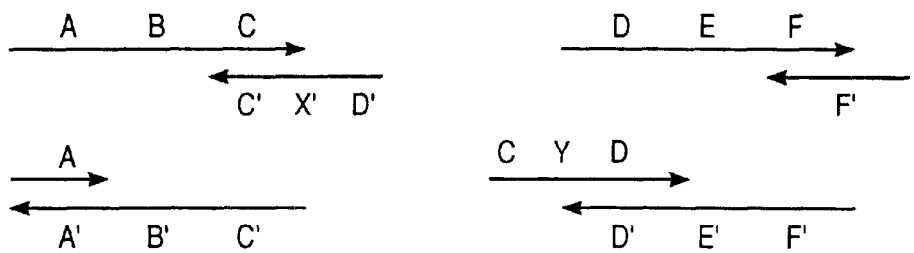
EXTEND AND MELT
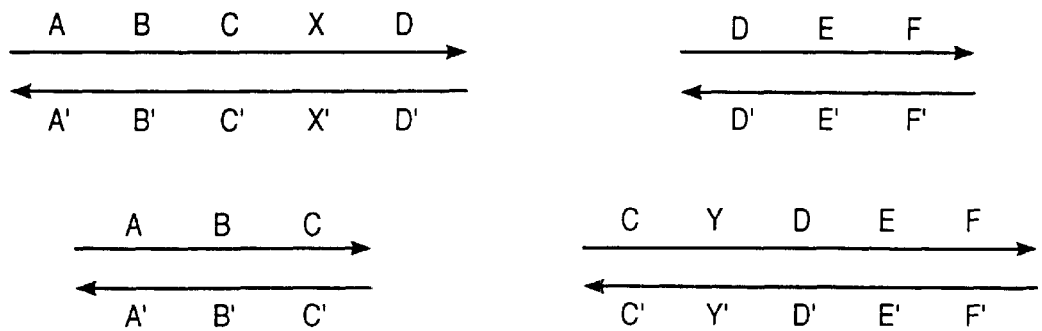
FIG. 10A EXTEND — AFTER A PERIOD, ASSUMING EQUIMOLAR PRIMERS, ONLY THE FOLLOWING PRODUCTS ARE LEFT.
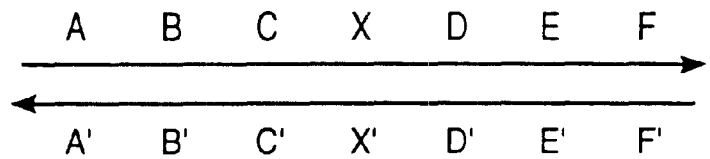
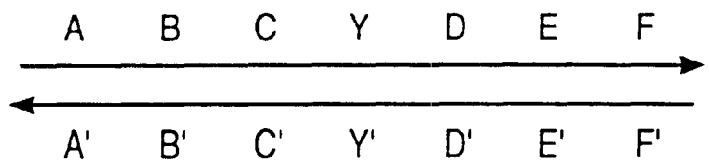
AMPLIFY USING ONLY PRIMERS A AND F'
IF NECESSARY, DIGEST TO SEPARATE THE COMPONENTS USING RESTRICTION SITES INCORPORATED INTO X AND Y
FIG. 10C

INITIAL CONDITIONS:
SEQUENCE EMBEDDED IN GENOME DNA, INDICATED IN GRAY.
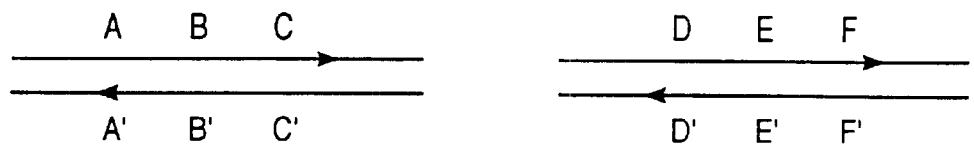
ANNEAL #1:
LOW CONCENTRATION STANDARD REGULAR PCR PRIMERS.
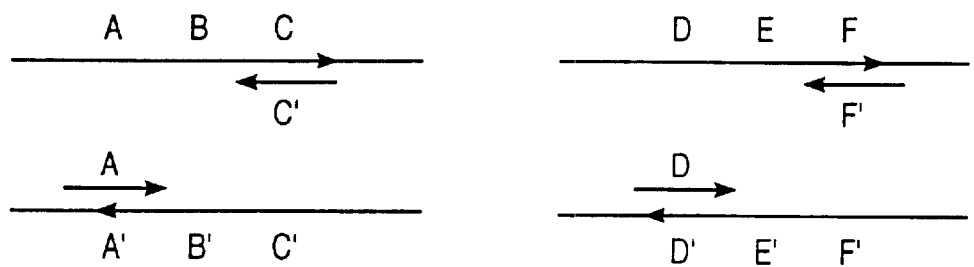
FIG. 11A

ANNEAL WITH PRIMERS:
NEW PRIMERS ARE AT HIGHER CONCENTRATION THAN INITIAL PRIMERS SO THAT THERE IS NO COMPETITION WITH THESE PRIMERS BINDING WITH THE INITIAL PRIMERS. NOTE THAT PRIMERS ARE SELECTED FOR ONLY ONE STRAND. THE ORIENTATION IS SELECTED SO THAT THE RESULTING FRAGMENT OVERLAP
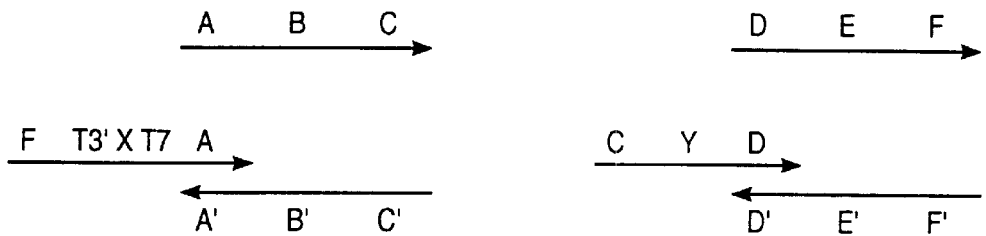
EXTEND AND MELT:
FIG. 11B

REANNEAL
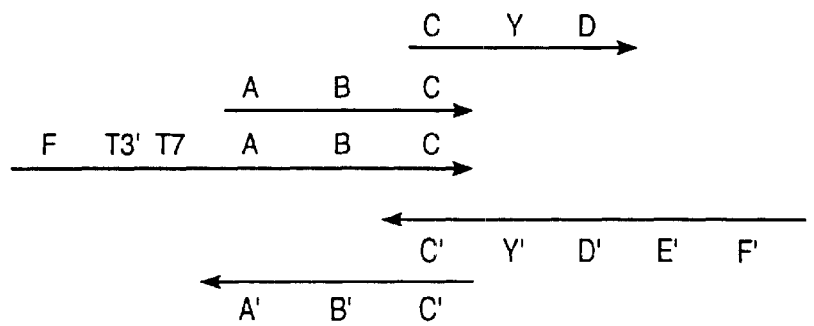
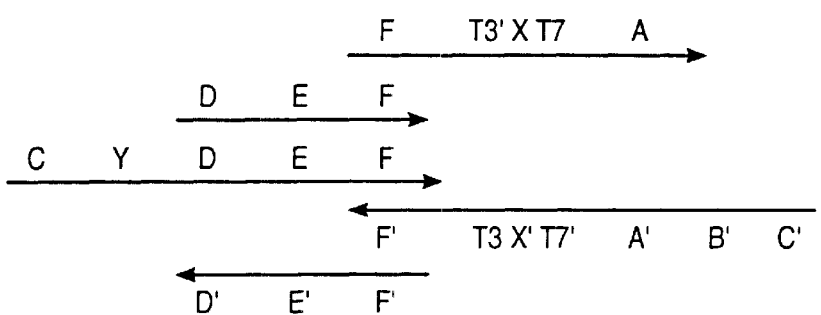
EXTEND
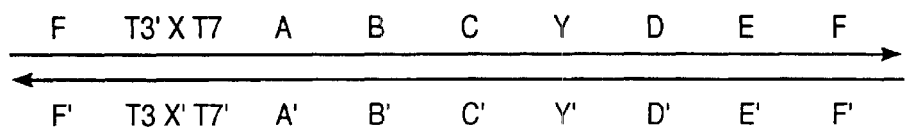
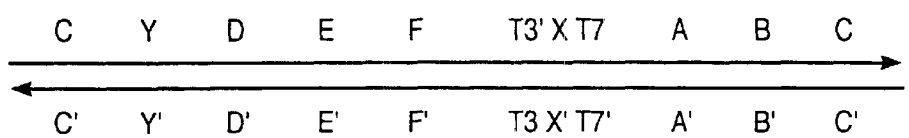
FIG. 11C

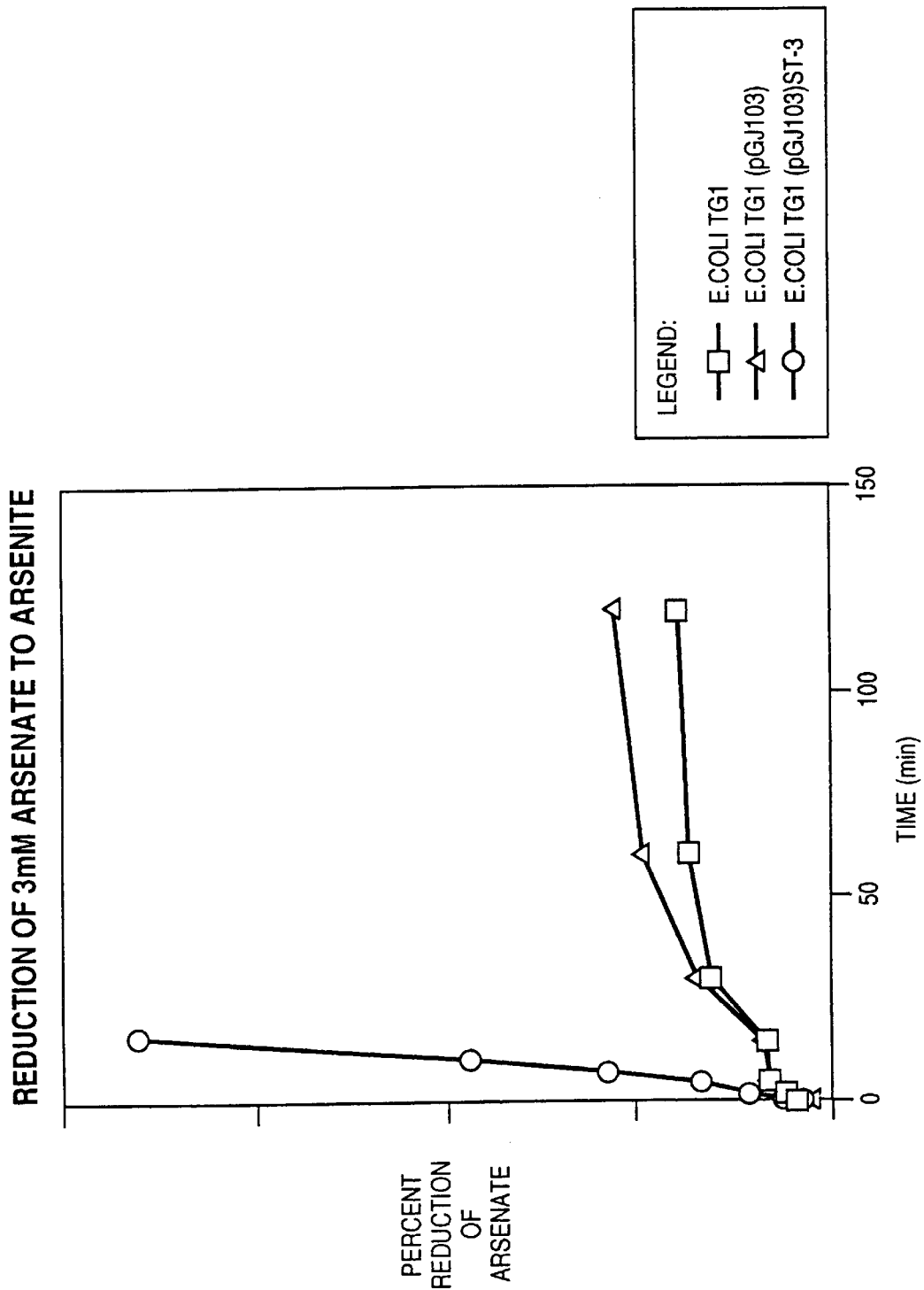

SEQUENCE LISTING (1) GENERAL INFORMATION:

(iii) NUMBER OF SEQUENCES: 136

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:1:

AAAGCGTCGA TTTTTGTGAT                                    20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:2:

ATGGGGTTCC GCGCACATTT                                    20

(2) INFORMATION FOR SEQ ID NO:3:

(i) SEQUENCE CHARACTERISTICS:
      (A) LENGTH: 40 base pairs
      (B) TYPE: nucleic acid
      (C) STRANDEDNESS: double
      (D) TOPOLOGY: circular (xi) SEQUENCE DESCRIPTION: SEQ ID NO:3:

CTCACGTTAA GGGATTTTGG TCATGAGATT ATCAAAAAGG                    40

(2) INFORMATION FOR SEQ ID NO:4:

(i) SEQUENCE CHARACTERISTICS:
      (A) LENGTH: 40 base pairs
      (B) TYPE: nucleic acid
      (C) STRANDEDNESS: double
      (D) TOPOLOGY: circular (xi) SEQUENCE DESCRIPTION: SEQ ID NO:4:

ATCTTCACCT AGATCCTTTT AAATTAAAAA TGAAGTTTTA                    40

(2) INFORMATION FOR SEQ ID NO:5:

(i) SEQUENCE CHARACTERISTICS:
      (A) LENGTH: 40 base pairs
      (B) TYPE: nucleic acid
      (C) STRANDEDNESS: single
      (D) TOPOLOGY: circular (xi) SEQUENCE DESCRIPTION: SEQ ID NO:5:

AATCAATCTA AAGTATATAT GAGGCCTGAC AGGCCGGTCT                    40

(2) INFORMATION FOR SEQ ID NO:6:

(i) SEQUENCE CHARACTERISTICS:
      (A) LENGTH: 40 base pairs
      (B) TYPE: nucleic acid
      (C) STRANDEDNESS: double (D) TOPOLOGY: circular (xi) SEQUENCE DESCRIPTION: SEQ ID NO:6:

GACAGTTACC AATGCTTAAT CAGTGAGGCA CCTATCTCAG                       40

(2) INFORMATION FOR SEQ ID NO:7:

(i) SEQUENCE CHARACTERISTICS:
           (A) LENGTH: 40 base pairs
           (B) TYPE: nucleic acid
           (C) STRANDEDNESS: double
           (D) TOPOLOGY: circular (xi) SEQUENCE DESCRIPTION: SEQ ID NO:7:

CGATCTGTCT ATTTCGTTCA TCCATGGTTG CCTGACTCCC                       40

(2) INFORMATION FOR SEQ ID NO:8:

(i) SEQUENCE CHARACTERISTICS:
           (A) LENGTH: 40 base pairs
           (B) TYPE: nucleic acid
           (C) STRANDEDNESS: double
           (D) TOPOLOGY: circular (xi) SEQUENCE DESCRIPTION: SEQ ID NO:8:

CGTCGTGTAG ATAACTACGA TACGGGAGGG CTTACCATCT                       40

(2) INFORMATION FOR SEQ ID NO:9:

(i) SEQUENCE CHARACTERISTICS:
           (A) LENGTH: 40 base pairs
           (B) TYPE: nucleic acid
           (C) STRANDEDNESS: double
           (D) TOPOLOGY: circular (xi) SEQUENCE DESCRIPTION: SEQ ID NO:9:

GGCCCCAGTG CTGCAATGAT ACCGCGAGAC CCACGCTCAC                       40

(2) INFORMATION FOR SEQ ID NO:10:

(i) SEQUENCE CHARACTERISTICS:
           (A) LENGTH: 40 base pairs
           (B) TYPE: nucleic acid
           (C) STRANDEDNESS: double
           (D) TOPOLOGY: circular (xi) SEQUENCE DESCRIPTION: SEQ ID NO:10:

CGGCTCCAGA TTTATCAGCA ATAAACCAGC CAGCTGGAAG                       40

(2) INFORMATION FOR SEQ ID NO:11:

(i) SEQUENCE CHARACTERISTICS:
           (A) LENGTH: 40 base pairs
           (B) TYPE: nucleic acid
           (C) STRANDEDNESS: double
           (D) TOPOLOGY: circular (xi) SEQUENCE DESCRIPTION: SEQ ID NO:11:

GGCCGAGCGC AGAAGTGGTC CTGCAACTTT ATCCGCCTCC                       40

(2) INFORMATION FOR SEQ ID NO:12:

(i) SEQUENCE CHARACTERISTICS:
           (A) LENGTH: 40 base pairs
           (B) TYPE: nucleic acid
           (C) STRANDEDNESS: double
           (D) TOPOLOGY: circular (xi) SEQUENCE DESCRIPTION: SEQ ID NO:12:

ATCCAGTCTA TTAATTGTTG CCGGGAAGCT AGAGTAAGTA                    40

(2) INFORMATION FOR SEQ ID NO:13:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:13:

GTTCGCCAGT TAATAGTTTG CGCAACGTTG TTGCCATGGC                    40

(2) INFORMATION FOR SEQ ID NO:14:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:14:

TACAGGCATC GTGGTGTCAC GCTCGTCGTT TGGAATGGCT                    40

(2) INFORMATION FOR SEQ ID NO:15:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:15:

TCATTCAGCT CCGGTTCCCA ACGATCAAGG CGAGTTACAT                    40

(2) INFORMATION FOR SEQ ID NO:16:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:16:

GATCCCCCAT GTTGTGCAAA AAAGCGGTTA GCTCCTTCGG                    40

(2) INFORMATION FOR SEQ ID NO:17:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:17:

TCCTCCGATG CTTGTCAGAA GTAAGTTGGC TGCAGTGTTA                    40

(2) INFORMATION FOR SEQ ID NO:18:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:18:

TCACTCATGG TTATGGCAGC ACTGCATAAT TCTCTTACTG                                40

(2) INFORMATION FOR SEQ ID NO:19:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:19:

TCATGCCATC CGTAAGATGC TTTTCTGTGA CTGGTGAGTA                                40

(2) INFORMATION FOR SEQ ID NO:20:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:20:

CTCAACCAAG TCATTCTGAG AATAGTGTAT GCGGCGACCG                                40

(2) INFORMATION FOR SEQ ID NO:21:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:21:

AGTTGCTCTT GCCCGGCGTC AATACGGGAT AATACCGCGC                                40

(2) INFORMATION FOR SEQ ID NO:22:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:22:

CACATAGCAG AACTTTAAAA GTGCTCATCA TTGGAAAACG                                40

(2) INFORMATION FOR SEQ ID NO:23:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:23:

TTCTTCGGGG CGAAAACTCT CAAGGATCTT ACCGCTGTTG                                40

(2) INFORMATION FOR SEQ ID NO:24:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:24:

AGATCCAGTT CGATGTAACC CACTCGTGCA CCCAACTGAT                40

(2) INFORMATION FOR SEQ ID NO:25:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:25:

CTTCAGCATC TTTTACTTTC ACCAGCGTTT CTGGGTGAGC                40

(2) INFORMATION FOR SEQ ID NO:26:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:26:

AAAAACAGGA AGGCAAAATG CCGCAAAAAA GGGAATAAGG                40

(2) INFORMATION FOR SEQ ID NO:27:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:27:

GCGACACGGA AATGTTGAAT ACTCATACTC TTCCTTTTTC                40

(2) INFORMATION FOR SEQ ID NO:28:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:28:

AATATTATTG AAGCATTTAT CAGGGTTATT GTCTCATGAG                40

(2) INFORMATION FOR SEQ ID NO:29:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:29:

CGGATACATA TTTGAATGTA TTTAGGCCAT GGTGGCCAAA                40

(2) INFORMATION FOR SEQ ID NO:30:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:30:

AATAAACAAA TAGGGGTTCC GCGCACATTT CCCCGAAAAG                               40

(2) INFORMATION FOR SEQ ID NO:31:

(i) SEQUENCE CHARACTERISTICS:
       (A) LENGTH: 40 base pairs
       (B) TYPE: nucleic acid
       (C) STRANDEDNESS: double
       (D) TOPOLOGY: circular (xi) SEQUENCE DESCRIPTION: SEQ ID NO:31:

TTCTTAGACG TCAGGTGGCA CTTTTCGGGG AAATGTGCGC                               40

(2) INFORMATION FOR SEQ ID NO:32:

(i) SEQUENCE CHARACTERISTICS:
       (A) LENGTH: 40 base pairs
       (B) TYPE: nucleic acid
       (C) STRANDEDNESS: double
       (D) TOPOLOGY: circular (xi) SEQUENCE DESCRIPTION: SEQ ID NO:32:

GGAACCCCTA TTTGTTTATT TTTGGCCACC ATGGCCTAAA                               40

(2) INFORMATION FOR SEQ ID NO:33:

(i) SEQUENCE CHARACTERISTICS:
       (A) LENGTH: 40 base pairs
       (B) TYPE: nucleic acid
       (C) STRANDEDNESS: double
       (D) TOPOLOGY: circular (xi) SEQUENCE DESCRIPTION: SEQ ID NO:33:

TACATTCAAA TATGTATCCG CTCATGAGAC AATAACCCTG                               40

(2) INFORMATION FOR SEQ ID NO:34:

(i) SEQUENCE CHARACTERISTICS:
       (A) LENGTH: 40 base pairs
       (B) TYPE: nucleic acid
       (C) STRANDEDNESS: double
       (D) TOPOLOGY: circular (xi) SEQUENCE DESCRIPTION: SEQ ID NO:34:

ATAAATGCTT CAATAATATT GAAAAAGGAA GAGTATGAGT                               40

(2) INFORMATION FOR SEQ ID NO:35:

(i) SEQUENCE CHARACTERISTICS:
       (A) LENGTH: 40 base pairs
       (B) TYPE: nucleic acid
       (C) STRANDEDNESS: double
       (D) TOPOLOGY: circular (xi) SEQUENCE DESCRIPTION: SEQ ID NO:35:

ATTCAACATT TCCGTGTCGC CCTTATTCCC TTTTTTGCGG                               40

(2) INFORMATION FOR SEQ ID NO:36:

(i) SEQUENCE CHARACTERISTICS:
       (A) LENGTH: 40 base pairs
       (B) TYPE: nucleic acid
       (C) STRANDEDNESS: double
       (D) TOPOLOGY: circular (xi) SEQUENCE DESCRIPTION: SEQ ID NO:36:

CATTTTGCCT TCCTGTTTTT GCTCACCCAG AAACGCTGGT                               40

(2) INFORMATION FOR SEQ ID NO:37:

(i) SEQUENCE CHARACTERISTICS:
  (A) LENGTH: 40 base pairs
  (B) TYPE: nucleic acid
  (C) STRANDEDNESS: double
  (D) TOPOLOGY: circular (xi) SEQUENCE DESCRIPTION: SEQ ID NO:37:

GAAAGTAAAA GATGCTGAAG ATCAGTTGGG TGCACGAGTG     40

(2) INFORMATION FOR SEQ ID NO:38:

(i) SEQUENCE CHARACTERISTICS:
  (A) LENGTH: 40 base pairs
  (B) TYPE: nucleic acid
  (C) STRANDEDNESS: double
  (D) TOPOLOGY: circular (xi) SEQUENCE DESCRIPTION: SEQ ID NO:38:

GGTTACATCG AACTGGATCT CAACAGCGGT AAGATCCTTG     40

(2) INFORMATION FOR SEQ ID NO:39:

(i) SEQUENCE CHARACTERISTICS:
  (A) LENGTH: 40 base pairs
  (B) TYPE: nucleic acid
  (C) STRANDEDNESS: double
  (D) TOPOLOGY: circular (xi) SEQUENCE DESCRIPTION: SEQ ID NO:39:

AGAGTTTTCG CCCCGAAGAA CGTTTTCCAA TGATGAGCAC     40

(2) INFORMATION FOR SEQ ID NO:40:

(i) SEQUENCE CHARACTERISTICS:
  (A) LENGTH: 40 base pairs
  (B) TYPE: nucleic acid
  (C) STRANDEDNESS: double
  (D) TOPOLOGY: circular (xi) SEQUENCE DESCRIPTION: SEQ ID NO:40:

TTTTAAAGTT CTGCTATGTG GCGCGGTATT ATCCCGTATT     40

(2) INFORMATION FOR SEQ ID NO:41:

(i) SEQUENCE CHARACTERISTICS:
  (A) LENGTH: 40 base pairs
  (B) TYPE: nucleic acid
  (C) STRANDEDNESS: double
  (D) TOPOLOGY: circular (xi) SEQUENCE DESCRIPTION: SEQ ID NO:41:

GACGCCGGGC AAGAGCAACT CGGTCGCCGC ATACACTATT     40

(2) INFORMATION FOR SEQ ID NO:42:

(i) SEQUENCE CHARACTERISTICS:
  (A) LENGTH: 40 base pairs
  (B) TYPE: nucleic acid
  (C) STRANDEDNESS: double
  (D) TOPOLOGY: circular (xi) SEQUENCE DESCRIPTION: SEQ ID NO:42:

CTCAGAATGA CTTGGTTGAG TACTCACCAG TCACAGAAAA     40

(2) INFORMATION FOR SEQ ID NO:43:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:43:

GCATCTTACG GATGGCATGA CAGTAAGAGA ATTATGCAGT        40

(2) INFORMATION FOR SEQ ID NO:44:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:44:

GCTGCCATAA CCATGAGTGA TAACACTGCA GCCAACTTAC        40

(2) INFORMATION FOR SEQ ID NO:45:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:45:

TTCTGACAAC GATCGGAGGA CCGAAGGAGC TAACCGCTTT        40

(2) INFORMATION FOR SEQ ID NO:46:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:46:

TTTGCACAAC ATGGGGATC ATGTAACTCG CCTTGATCGT        40

(2) INFORMATION FOR SEQ ID NO:47:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:47:

TGGGAACCGG AGCTGAATGA AGCCATTCCA AACGACGAGC        40

(2) INFORMATION FOR SEQ ID NO:48:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:48:

GTGACACCAC GATGCCTGTA GCCATGGCAA CAACGTTGCG        40

(2) INFORMATION FOR SEQ ID NO:49:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:49:

CAAACTATTA ACTGGCGAAC TACTTACTCT AGCTTCCCGG                              40

(2) INFORMATION FOR SEQ ID NO:50:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:50:

CAACAATTAA TAGACTGGAT GGAGGCGGAT AAAGTTGCAG                              40

(2) INFORMATION FOR SEQ ID NO:51:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:51:

GACCACTTCT GCGCTCGGCC CTTCCAGCTG GCTGGTTTAT                              40

(2) INFORMATION FOR SEQ ID NO:52:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:52:

TGCTGATAAA TCTGGAGCCG GTGAGCGTGG GTCTCGCGGT                              40

(2) INFORMATION FOR SEQ ID NO:53:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:53:

ATCATTGCAG CACTGGGGCC AGATGGTAAG CCCTCCCGTA                              40

(2) INFORMATION FOR SEQ ID NO:54:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:54:

TCGTAGTTAT CTACACGACG GGGAGTCAGG CAACCATGGA                              40

(2) INFORMATION FOR SEQ ID NO:55:

(i) SEQUENCE CHARACTERISTICS:
    (A) LENGTH: 40 base pairs
    (B) TYPE: nucleic acid
    (C) STRANDEDNESS: double
    (D) TOPOLOGY: circular (xi) SEQUENCE DESCRIPTION: SEQ ID NO:55:

TGAACGAAAT AGACAGATCG CTGAGATAGG TGCCTCACTG                    40

(2) INFORMATION FOR SEQ ID NO:56:

(i) SEQUENCE CHARACTERISTICS:
       (A) LENGTH: 40 base pairs
       (B) TYPE: nucleic acid
       (C) STRANDEDNESS: double
       (D) TOPOLOGY: circular (xi) SEQUENCE DESCRIPTION: SEQ ID NO:56:

ATTAAGCATT GGTAACTGTC AGACCGGCCT GTCAGGCCTC                    40

(2) INFORMATION FOR SEQ ID NO:57:

(i) SEQUENCE CHARACTERISTICS:
       (A) LENGTH: 40 base pairs
       (B) TYPE: nucleic acid
       (C) STRANDEDNESS: double
       (D) TOPOLOGY: circular (xi) SEQUENCE DESCRIPTION: SEQ ID NO:57:

ATATATACTT TAGATTGATT TAAAACTTCA TTTTTAATTT                    40

(2) INFORMATION FOR SEQ ID NO:58:

(i) SEQUENCE CHARACTERISTICS:
       (A) LENGTH: 40 base pairs
       (B) TYPE: nucleic acid
       (C) STRANDEDNESS: double
       (D) TOPOLOGY: circular (xi) SEQUENCE DESCRIPTION: SEQ ID NO:58:

AAAAGGATCT AGGTGAAGAT CCTTTTTGAT AATCTCATGA                    40

(2) INFORMATION FOR SEQ ID NO:59:

(i) SEQUENCE CHARACTERISTICS:
       (A) LENGTH: 40 base pairs
       (B) TYPE: nucleic acid
       (C) STRANDEDNESS: double
       (D) TOPOLOGY: circular (xi) SEQUENCE DESCRIPTION: SEQ ID NO:59:

GGAAAACCCT GGCGTTACCC AACTTAATCG CCTTGCAGCA                    40

(2) INFORMATION FOR SEQ ID NO:60:

(i) SEQUENCE CHARACTERISTICS:
       (A) LENGTH: 40 base pairs
       (B) TYPE: nucleic acid
       (C) STRANDEDNESS: double
       (D) TOPOLOGY: circular (xi) SEQUENCE DESCRIPTION: SEQ ID NO:60:

CATCCCCCTT TCGCCAGCTG GCGTAATAGC GAAGAGGCCC                    40

(2) INFORMATION FOR SEQ ID NO:61:

(i) SEQUENCE CHARACTERISTICS:
    (A) LENGTH: 40 base pairs
    (B) TYPE: nucleic acid
    (C) STRANDEDNESS: double
    (D) TOPOLOGY: circular (xi) SEQUENCE DESCRIPTION: SEQ ID NO:61:

GCACCGATCG CCCTTCCCAA CAGTTGCGTA GCCTGAATGG                     40

(2) INFORMATION FOR SEQ ID NO:62:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:62:

CGAATGGCGC CTGATGCGGT ATTTTCTCCT TACGCATCTG                     40

(2) INFORMATION FOR SEQ ID NO:63:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:63:

TGCGGTATTT CACACCGCAT ATGGTGCACT CTCAGTACAA                     40

(2) INFORMATION FOR SEQ ID NO:64:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:64:

TCTGCTCTGA TGCCGCATAG TTAAGCCAGC CCCGACACCC                     40

(2) INFORMATION FOR SEQ ID NO:65:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:65:

GCCAACACCC GCTGACGCGC CCTGACGGGC TTGTCTGCTC                     40

(2) INFORMATION FOR SEQ ID NO:66:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:66:

CCGGCATCCG CTTACAGACA AGCTGTGACC GTCTCCGGGA                     40

(2) INFORMATION FOR SEQ ID NO:67:

(i) SEQUENCE CHARACTERISTICS:

(A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:67:

GCTGCATGTG TCAGAGGTTT TCACCGTCAT CACCGAAACG                                    40

(2) INFORMATION FOR SEQ ID NO:68:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:68:

CGAGGCCCTT TCGTCTCGCG CGTTTCGGTG ATGACGGTGA                                    40

(2) INFORMATION FOR SEQ ID NO:69:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:69:

AAACCTCTGA CACATGCAGC TCCCGGAGAC GGTCACAGCT                                    40

(2) INFORMATION FOR SEQ ID NO:70:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:70:

TGTCTGTAAG CGGATGCCGG GAGCAGACAA GCCCGTCAGG                                    40

(2) INFORMATION FOR SEQ ID NO:71:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:71:

GCGCGTCAGC GGGTGTTGGC GGGTGTCGGG GCTGGCTTAA                                    40

(2) INFORMATION FOR SEQ ID NO:72:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:72:

CTATGCGGCA TCAGAGCAGA TTGTACTGAG AGTGCACCAT                                    40

(2) INFORMATION FOR SEQ ID NO:73:

(i) SEQUENCE CHARACTERISTICS:
        (A) LENGTH: 40 base pairs (B) TYPE: nucleic acid
        (C) STRANDEDNESS: double
        (D) TOPOLOGY: circular (xi) SEQUENCE DESCRIPTION: SEQ ID NO:73:

ATGCGGTGTG AAATACCGCA CAGATGCGTA AGGAGAAAAT                              40

(2) INFORMATION FOR SEQ ID NO:74:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:74:

ACCGCATCAG GCGCCATTCG CCATTCAGGC TACGCAACTG                              40

(2) INFORMATION FOR SEQ ID NO:75:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:75:

TTGGGAAGGG CGATCGGTGC GGGCCTCTTC GCTATTACGC                              40

(2) INFORMATION FOR SEQ ID NO:76:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:76:

CAGCTGGCGA AAGGGGGATG TGCTGCAAGG CGATTAAGTT                              40

(2) INFORMATION FOR SEQ ID NO:77:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:77:

GGGTAACGCC AGGGTTTTCC CAGTCACGAC GTTGTAAAAC                              40

(2) INFORMATION FOR SEQ ID NO:78:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:78:

GACGGCCAGT GCCAAGCTTG CATGCCTGCA GGTCGACTCT                              40

(2) INFORMATION FOR SEQ ID NO:79:

(i) SEQUENCE CHARACTERISTICS:
        (A) LENGTH: 40 base pairs
        (B) TYPE: nucleic acid

```
        (C) STRANDEDNESS: double
        (D) TOPOLOGY: circular (xi) SEQUENCE DESCRIPTION: SEQ ID NO:79:

AGAGGATCCC CGGGTACCGA GCTCGAATTC GTAATCATGG                              40

(2) INFORMATION FOR SEQ ID NO:80:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:80:

TCATAGCTGT TTCCTGTGTG AAATTGTTAT CCGCTCACAA                              40

(2) INFORMATION FOR SEQ ID NO:81:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:81:

TTCCACACAA CATACGAGCC GGAAGCATAA AGTGTAAAGC                              40

(2) INFORMATION FOR SEQ ID NO:82:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:82:

CTGGGGTGCC TAATGAGTGA GCTAACTCAC ATTAATTGCG                              40

(2) INFORMATION FOR SEQ ID NO:83:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:83:

TTGCGCTCAC TGCCCGCTTT CCAGTCGGGA AACCTGTCGT                              40

(2) INFORMATION FOR SEQ ID NO:84:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:84:

GCCAGCTGCA TTAATGAATC GGCCAACGCG CGGGGAGAGG                              40

(2) INFORMATION FOR SEQ ID NO:85:

(i) SEQUENCE CHARACTERISTICS:
        (A) LENGTH: 40 base pairs
        (B) TYPE: nucleic acid
        (C) STRANDEDNESS: double
```

(D) TOPOLOGY: circular (xi) SEQUENCE DESCRIPTION: SEQ ID NO:85:

CGGTTTGCGT ATTGGGCGCT CTTCCGCTTC CTCGCTCACT                              40

(2) INFORMATION FOR SEQ ID NO:86:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:86:

GACTCGCTGC GCTCGGTCGT TCGGCTGCGG CGAGCGGTAT                              40

(2) INFORMATION FOR SEQ ID NO:87:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:87:

CAGCTCACTC AAAGGCGGTA ATACGGTTAT CCACAGAATC                              40

(2) INFORMATION FOR SEQ ID NO:88:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:88:

AGGGGATAAC GCAGGAAAGA ACATGTGAGC AAAAGGCCAG                              40

(2) INFORMATION FOR SEQ ID NO:89:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:89:

CAAAAGGCCA GGAACCGTAA AAAGGCCGCG TTGCTGGCGT                              40

(2) INFORMATION FOR SEQ ID NO:90:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:90:

TTTTCCATAG GCTCCGCCCC CCTGACGAGC ATCACAAAAA                              40

(2) INFORMATION FOR SEQ ID NO:91:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:91:

TCGACGCTCA AGTCAGAGGT GGCGAAACCC GACAGGACTA                40

(2) INFORMATION FOR SEQ ID NO:92:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:92:

TAAAGATACC AGGCGTTTCC CCCTGGAAGC TCCCTCGTGC                40

(2) INFORMATION FOR SEQ ID NO:93:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:93:

GCTCTCCTGT TCCGACCCTG CCGCTTACCG GATACCTGTC                40

(2) INFORMATION FOR SEQ ID NO:94:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:94:

CGCCTTTCTC CCTTCGGGAA GCGTGGCGCT TTCTCAATGC                40

(2) INFORMATION FOR SEQ ID NO:95:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:95:

TCACGCTGTA GGTATCTCAG TTCGGTGTAG GTCGTTCGCT                40

(2) INFORMATION FOR SEQ ID NO:96:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:96:

CCAAGCTGGG CTGTGTGCAC GAACCCCCCG TTCAGCCCGA                40

(2) INFORMATION FOR SEQ ID NO:97:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:97:

CCGCTGCGCC TTATCCGGTA ACTATCGTCT TGAGTCCAAC                    40

(2) INFORMATION FOR SEQ ID NO:98:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:98:

CCGGTAAGAC ACGACTTATC GCCACTGGCA GCAGCCACTG                    40

(2) INFORMATION FOR SEQ ID NO:99:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:99:

GTAACAGGAT TAGCAGAGCG AGGTATGTAG GCGGTGCTAC                    40

(2) INFORMATION FOR SEQ ID NO:100:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:100:

AGAGTTCTTG AAGTGGTGGC CTAACTACGG CTACACTAGA                    40

(2) INFORMATION FOR SEQ ID NO:101:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:101:

AGGACAGTAT TTGGTATCTG CGCTCTGCTG AAGCCAGTTA                    40

(2) INFORMATION FOR SEQ ID NO:102:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:102:

CCTTCGGAAA AAGAGTTGGT AGCTCTTGAT CCGGCAAACA                    40

(2) INFORMATION FOR SEQ ID NO:103:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:103:

AACCACCGCT GGTAGCGGTG GTTTTTTTGT TTGCAAGCAG                    40

(2) INFORMATION FOR SEQ ID NO:104:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:104:

CAGATTACGC GCAGAAAAAA AGGATCTCAA GAAGATCCTT                    40

(2) INFORMATION FOR SEQ ID NO:105:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:105:

TGATCTTTTC TACGGGGTCT GACGCTCAGT GGAACGAAAA                    40

(2) INFORMATION FOR SEQ ID NO:106:

(i) SEQUENCE CHARACTERISTICS:
        (A) LENGTH: 56 base pairs
        (B) TYPE: nucleic acid
        (C) STRANDEDNESS: double
        (D) TOPOLOGY: circular (xi) SEQUENCE DESCRIPTION: SEQ ID NO:106:

CGCGAGACGA AAGGGCCTCG TGATACGCCT ATTTTTATAG GTTAATGTCA TGATAA    56

(2) INFORMATION FOR SEQ ID NO:107:

(i) SEQUENCE CHARACTERISTICS:
        (A) LENGTH: 47 base pairs
        (B) TYPE: nucleic acid
        (C) STRANDEDNESS: double
        (D) TOPOLOGY: circular (xi) SEQUENCE DESCRIPTION: SEQ ID NO:107:

TGCCACCTGA CGTCTAAGAA ACCATTATTA TCATGACATT AACCTAT            47

(2) INFORMATION FOR SEQ ID NO:108:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:108:

CCAAAATCCC TTAACGTGAG TTTTCGTTCC ACTGAGCGTC                    40

(2) INFORMATION FOR SEQ ID NO:109:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:109:

```
AGACCCCGTA GAAAAGATCA AAGGATCTTC TTGAGATCCT                              40

(2) INFORMATION FOR SEQ ID NO:110:

(i) SEQUENCE CHARACTERISTICS:
         (A) LENGTH: 40 base pairs
         (B) TYPE: nucleic acid
         (C) STRANDEDNESS: double
         (D) TOPOLOGY: circular (xi) SEQUENCE DESCRIPTION: SEQ ID NO:110:

TTTTTTCTGC GCGTAATCTG CTGCTTGCAA ACAAAAAAAC                              40

(2) INFORMATION FOR SEQ ID NO:111:

(i) SEQUENCE CHARACTERISTICS:
         (A) LENGTH: 40 base pairs
         (B) TYPE: nucleic acid
         (C) STRANDEDNESS: double
         (D) TOPOLOGY: circular (xi) SEQUENCE DESCRIPTION: SEQ ID NO:111:

CACCGCTACC AGCGGTGGTT TGTTTGCCGG ATCAAGAGCT                              40

(2) INFORMATION FOR SEQ ID NO:112:

(i) SEQUENCE CHARACTERISTICS:
         (A) LENGTH: 40 base pairs
         (B) TYPE: nucleic acid
         (C) STRANDEDNESS: double
         (D) TOPOLOGY: circular (xi) SEQUENCE DESCRIPTION: SEQ ID NO:112:

ACCAACTCTT TTTCCGAAGG TAACTGGCTT CAGCAGAGCG                              40

(2) INFORMATION FOR SEQ ID NO:113:

(i) SEQUENCE CHARACTERISTICS:
         (A) LENGTH: 40 base pairs
         (B) TYPE: nucleic acid
         (C) STRANDEDNESS: double
         (D) TOPOLOGY: circular (xi) SEQUENCE DESCRIPTION: SEQ ID NO:113:

CAGATACCAA ATACTGTCCT TCTAGTGTAG CCGTAGTTAG                              40

(2) INFORMATION FOR SEQ ID NO:114:

(i) SEQUENCE CHARACTERISTICS:
         (A) LENGTH: 40 base pairs
         (B) TYPE: nucleic acid
         (C) STRANDEDNESS: double
         (D) TOPOLOGY: circular (xi) SEQUENCE DESCRIPTION: SEQ ID NO:114:

GCCACCACTT CAAGAACTCT GTAGCACCGC CTACATACCT                              40

(2) INFORMATION FOR SEQ ID NO:115:

(i) SEQUENCE CHARACTERISTICS:
         (A) LENGTH: 40 base pairs
         (B) TYPE: nucleic acid
         (C) STRANDEDNESS: double
         (D) TOPOLOGY: circular (xi) SEQUENCE DESCRIPTION: SEQ ID NO:115:

CGCTCTGCTA ATCCTGTTAC CAGTGGCTGC TGCCAGTGGC                              40
```

(2) INFORMATION FOR SEQ ID NO:116:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:116:

GATAAGTCGT GTCTTACCGG GTTGGACTCA AGACGATAGT                        40

(2) INFORMATION FOR SEQ ID NO:117:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:117:

TACCGGATAA GGCGCAGCGG TCGGGCTGAA CGGGGGGTTC                        40

(2) INFORMATION FOR SEQ ID NO:118:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:118:

GTGCACACAG CCCAGCTTGG AGCGAACGAC CTACACCGAA                        40

(2) INFORMATION FOR SEQ ID NO:119:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:119:

CTGAGATACC TACAGCGTGA GCATTGAGAA AGCGCCACGC                        40

(2) INFORMATION FOR SEQ ID NO:120:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:120:

TTCCCGAAGG GAGAAAGGCG GACAGGTATC CGGTAAGCGG                        40

(2) INFORMATION FOR SEQ ID NO:121:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:121:

CAGGGTCGGA ACAGGAGAGC GCACGAGGGA GCTTCCAGGG                        40

(2) INFORMATION FOR SEQ ID NO:122:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:122:

GGAAACGCCT GGTATCTTTA TAGTCCTGTC GGGTTTCGCC                    40

(2) INFORMATION FOR SEQ ID NO:123:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:123:

ACCTCTGACT TGAGCGTCGA TTTTTGTGAT GCTCGTCAGG                    40

(2) INFORMATION FOR SEQ ID NO:124:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:124:

GGGGCGGAGC CTATGGAAAA ACGCCAGCAA CGCGGCCTTT                    40

(2) INFORMATION FOR SEQ ID NO:125:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:125:

TTACGGTTCC TGGCCTTTTG CTGGCCTTTT GCTCACATGT                    40

(2) INFORMATION FOR SEQ ID NO:126:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:126:

TCTTTCCTGC GTTATCCCCT GATTCTGTGG ATAACCGTAT                    40

(2) INFORMATION FOR SEQ ID NO:127:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:127:

TACCGCCTTT GAGTGAGCTG ATACCGCTCG CCGCAGCCGA                    40

(2) INFORMATION FOR SEQ ID NO:128:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:128:

ACGACCGAGC GCAGCGAGTC AGTGAGCGAG GAAGCGGAAG                    40

(2) INFORMATION FOR SEQ ID NO:129:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:129:

AGCGCCCAAT ACGCAAACCG CCTCTCCCCG CGCGTTGGCC                    40

(2) INFORMATION FOR SEQ ID NO:130:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:130:

GATTCATTAA TGCAGCTGGC ACGACAGGTT TCCCGACTGG                    40

(2) INFORMATION FOR SEQ ID NO:131:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:131:

AAAGCGGGCA GTGAGCGCAA CGCAATTAAT GTGAGTTAGC                    40

(2) INFORMATION FOR SEQ ID NO:132:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:132:

TCACTCATTA GGCACCCCAG GCTTTACACT TTATGCTTCC                    40

(2) INFORMATION FOR SEQ ID NO:133:

(i) SEQUENCE CHARACTERISTICS:
        (A) LENGTH: 40 base pairs
        (B) TYPE: nucleic acid
        (C) STRANDEDNESS: double
        (D) TOPOLOGY: circular (xi) SEQUENCE DESCRIPTION: SEQ ID NO:133:

GGCTCGTATG TTGTGTGGAA TTGTGAGCGG ATAACAATTT                    40

(2) INFORMATION FOR SEQ ID NO:134:

```
        (i) SEQUENCE CHARACTERISTICS:
            (A) LENGTH: 40 base pairs
            (B) TYPE: nucleic acid
            (C) STRANDEDNESS: double
            (D) TOPOLOGY: circular (xi) SEQUENCE DESCRIPTION: SEQ ID NO:134:

CACACAGGAA ACAGCTATGA CCATGATTAC GAATTCGAGC                              40

(2) INFORMATION FOR SEQ ID NO:135:

(i) SEQUENCE CHARACTERISTICS:
            (A) LENGTH: 40 base pairs
            (B) TYPE: nucleic acid
            (C) STRANDEDNESS: double
            (D) TOPOLOGY: circular (xi) SEQUENCE DESCRIPTION: SEQ ID NO:135:

TCGGTACCCG GGGATCCTCT AGAGTCGACC TGCAGGCATG                              40

(2) INFORMATION FOR SEQ ID NO:136:

(i) SEQUENCE CHARACTERISTICS:
            (A) LENGTH: 40 base pairs
            (B) TYPE: nucleic acid
            (C) STRANDEDNESS: double
            (D) TOPOLOGY: circular (xi) SEQUENCE DESCRIPTION: SEQ ID NO:136:

CAAGCTTGGC ACTGGCCGTC GTTTTACAAC GTCGTGACTG                              40
```

END-COMPLEMENTARY POLYMERASE REACTION

This application is a continuation of Ser. No 08/675,502 filed Jul. 3, 1996 now U.S. Pat. No. 5,928,805 which was a continuation-in-part of and Ser. No. 08/425,684 filed Apr. 18, 1995, now U.S. Pat. No. 5,834,252 and a continuation from PCT/US96/05480 filed Apr. 18, 1996, the disclosures of which are incorporated by reference.

TECHNICAL FIELD

The present invention relates generally to the field of recombinant DNA technology and, more particularly, to improved methods for producing amplified heterogeneous populations of polynucleotides from limited quantities of DNA or RNA or other nucleic acids. The invention provides compositions and methods for a chain reaction amplification of a target polynucleotide species using a thermostable polymerase or other suitable polynucleotide polymerase compatible with the method.

BACKGROUND

Selective amplification of polynucleotides represents a major research goal of molecular biology, with particular importance in diagnostic and forensic applications, as well as for general manipulations of genetic materials and laboratory reagents.

The polymerase chain reaction (PCR) is a method by which a specific polynucleotide sequence can be amplified in vitro. PCR is an extremely powerful technique for amplifying specific polynucleotide sequences, including genomic DNA, single-stranded cDNA, and mRNA among others. As described in U.S. Pat. Nos. 4,683,202, 4,683,195, and 4,800,159 (which are incorporated herein by reference), PCR typically comprises treating separate complementary strands of a target nucleic acid with two oligonucleotide primers to form complementary primer extension products on both strands that act as templates for synthesizing copies of the desired nucleic acid sequences. By repeating the separation and synthesis steps in an automated system, essentially exponential duplication of the target sequences can be achieved.

A number of variations of the basic PCR methodology have been described. U.S. Pat. No. 5,066,584 discloses a method wherein single stranded DNA can be generated by the polymerase chain reaction using two oligonucleotide primers, one present in a limiting concentration. U.S. Pat. No. 5,340,728 discloses an improved method for performing a nested polymerase chain reaction (PCR) amplification of a targeted piece of DNA, wherein by controlling the annealing times and concentration of both the outer and the inner set of primers according to the method disclosed, highly specific and efficient amplification of a targeted piece of DNA can be achieved without depletion or removal of the outer primers from the reaction mixture vessel. U.S. Pat. No. 5,286,632 discloses recombination PCR (RPCR) wherein PCR is used with at least two primer species to add double-stranded homologous ends to DNA such that the homologous ends undergo in vivo recombination following transfection of host cells.

Horton et al. (1989) Gene 77: 61, discloses a method for making chimeric genes using PCR to generate overlapping homologous regions. In the Horton method, fragments of different genes that are to form the chimeric gene are generated in separate polymerase chain reactions. The primers used in these separate reactions are designed so that the ends of the different products of the separate reactions contain complementary sequences. When these separately produced PCR products are mixed, denatured and reannealed, the strands having matching sequences at their 3'-ends overlap and act as primers for each other. Extension of this overlap by DNA polymerase produces a molecule in which the original sequences are spliced together to form the chimeric gene.

Silver and Keerikatte (1989) *J. Virol.* 63: 1924 describe another variation of the standard PCR approach (which requires oligonucleotide primers complementary to both ends of the segment to be amplified) to allow amplification of DNA flanked on only one side by a region of known DNA sequence. This technique requires the presence of a known restriction site within the known DNA sequence and a similar site within the unknown flanking DNA sequence which is to be amplified. After restriction and recircularization, the recircularized fragment is restricted at an unique site between the two primers and the resulting linearized fragment is used as a template for PCR amplification.

Triglia et al. (1988) *Nucl.Acids Res.* 16: 8186, describe an approach which requires the inversion of the sequence of interest by circularization and re-opening at a site distinct from the one of interest, and is called "inverted PCR." A fragment is first created in which two unknown sequences flank on either side a region of known DNA sequence. The fragment is then circularized and cleaved with an unique restriction endonuclease which only cuts within the known DNA sequence creating a new fragment containing all of the DNA of the original fragment but which is then inverted with regions of known sequence flanking the region of unknown sequence. This fragment is then utilized as a PCR substrate to amplify the unknown sequence.

Vallette et al. (1989) *Nucl.Acids Res.* 17: 723 disclose using PCR in a specific approach which involves using a supercoiled plasmid DNA as a template for PCR and a primer bearing a mutated sequence which is incorporated into the amplified product. Using this method, DNA sequences may be inserted only at the 5'-end of the DNA molecule which one wishes to alter. Mole et al. (1989) *Nucl.Acids Res.* 17: 3319, used PCR to create deletions within existing expression plasmids. However, PCR was performed around the entire plasmid (containing the fragment to be deleted) from primers whose 5'-ends defined the region to be deleted. Self-ligation of the PCR product recircularized the plasmid.

U.S. Pat. No. 5,279,952 discloses a method for using PCR to generate mutations (e.g., deletions) and chimeric genes by forming head-to-tail concatemers of a known starting sequence and employing at least two PCR primers to amplify a DNA segment which is altered as compared to the known starting sequence.

Jones and Howard (1990) *BioTechniques* 8: 178, report a site-specific mutagenesis method using PCR, termed recombinant circle PCR (RCPCR). In RCPCR, separate PCR amplifications (typically two) of a known polynucleotide generate products that, when combined, denatured, and annealed, form double-stranded DNA with discrete, cohesive single-stranded ends designed so that they may anneal and form circles of DNA.

Oliner et al. (1993) *Nucl. Acids. Res.* 21: 5192, report a method for engineering PCR products to contain terminal sequences identical to sequences at the two ends of a linearized vector such that co-transfection of the PCR product and linearized vector into a recombination-competent host cell results in formation of a covalently linked vector containing the PCR product, thus avoiding the need for in vitro ligation.

In spite of such recent advances, including PCR and its various modifications noted above, there exists a need for improved methods of identifying and cloning polynucleotides, for accurate in vitro amplification of selected polynucleotides, and for facile assembly of polynucleotides from a mixture of component oligonucleotides or polynucleotides without necessitating the use of DNA ligase. In particular, there is a need for a PCR amplification method which can be performed with (1) only a single primer species, or (2) with multiple overlapping polynucleotide fragments (or oligonucleotides) in the absence of a conventional PCR primer, and which can result in formation of an amplified product which can be a concatemer and/or which can be a covalently-closed circle. The present invention fulfills these and other needs.

The references discussed herein are provided solely for their disclosure prior to the filing date of the present application. Nothing herein is to be construed as an admission that the inventors are not entitled to antedate such disclosure by virtue of prior invention. All publications cited are incorporated herein by reference.

SUMMARY OF THE INVENTION

A basis of the present invention is the use of polymerase-mediated chain extension, such as for example PCR, in combination with at least two polynucleotides having complementary ends which can anneal whereby at least one of said polynucleotides has a free 3'-hydroxyl capable of polynucleotide chain elongation by a DNA polymerase, such as a thermostable polymerase (e.g., *Thermus apuaticus* (Taq) polymerase or *Thermococcus litoralis* (Vent™, New England Biolabs) polymerase or TthI polymerase (Perkin-Elmer). Although the method can be practiced using PCR, in some embodiments either a single primer species or no primer whatsoever is required, and hence PCR is not a necessary component of the general method.

In one embodiment, a target polynucleotide is contacted with a "bivalent primer" typically comprising an oligonucleotide having two regions of complementarity to the target polynucleotide: (1) a first portion which is in the 5' portion of the primer and which is substantially complementary to a sequence in the 5'-portion of the sequence to be amplified (target sequence) in the target polynucleotide, and (2) a second portion which is in the 3' portion of the primer and which is substantially complementary to a sequence in the 3'-portion of the sequence to be amplified (target sequence) in the target polynucleotide. The contacting is performed under conditions suitable for hybridization of the bivalent primer to the target polynucleotide, most often following thermal denaturation of the target polynucleotide if it is initially present as a double-stranded form. The target polynucleotide may be substantially homogeneous or may be present in a mixture of polynucleotide species (e.g., in a genome, biological sample, or mixture of synthetic polynucleotides). Subsequent or concomitant with the contacting of the bivalent primer to the target polynucleotide, a polynucleotide polymerase, such as a thermostable DNA polymerase, catalyzes, under suitable reaction conditions, polynucleotide synthesis (chain elongation) primed from the 3'-hydroxyl of the annealed bivalent primer to form a strand complementary to the target sequence, thereby forming a nascent complementary strand. Following completion of the nascent complementary strand spanning the target sequence, the target polynucleotide and the nascent strand are denatured, typically by elevation of temperature, and allowed to reanneal, typically by reduction of temperature, with another molecule of the bivalent primer species or with a complementary strand of a target polynucleotide or an amplified copy thereof. The denatured nascent strand species following the first elongation cycle will contain a copy of the target sequence and has a terminal repeat of its 5'-terminal sequence at the 3' terminus, resulting from the bivalent primer, and wherein the terminal repeat is of sufficient length to support annealing under PCR conditions to an overlapping complementary strand in a head-to-tail arrangement (see, FIG. 1). Following reannealing, the described polymerase elongation/denaturation/reannealing cycle is repeated from 1 to about 100 times as desired, resulting in formation of amplified product which comprises head-to-tail concatemers of the target sequence. The concatemers typically increase in length as the number of amplification cycles increase and as the amount of bivalent primer decreases. Following amplification forming concatameric head-to-tail repeats of the target sequence, the concatemer(s) can optionally be resolved, such as (1) by cleaving with a restriction endonuclease which cuts within (or at the termini of) the concatemeric unit(s), (2) by homologous recombination between concatemer units to form covalently closed circles, or (3) by cleavage with a restriction endonuclease followed by ligation with DNA ligase to form covalently closed circles and/or by direct transformation into host cells for in vivo ligation.

Often, a target polynucleotide sequence which is amplified as described above will form amplification intermediates in the form of cyclized DNA or spiral DNA (see, FIG. 2), as a result of the 3' terminus of an overlapped nascent strand annealing to the 3' terminus of an overlapped complementary strand forming a cyclized structure similar to a gapped circle; the cyclized structure has a strand with an extendable 3'-hydroxyl which can be extended with a DNA polymerase substantially lacking exonuclease activity (e.g., a thermostable polymerase such as Vent(exo⁻)™ or Klenow fragment, etc.) in a rolling circle format whereby the leading terminus of the nascent strand continually displaces the lagging portion of the nascent strand (see, FIG. 2) producing a concatemeric single strand emanating from the rolling circle intermediate. Most often, such rolling circle intermediates will form under dilute conditions more favorable to intramolecular cyclization of overlapped strands. Once a rolling circle intermediate is established, the template need not be denatured in order to continue amplification of the target sequence as in conventional PCR, thus avoiding the necessity of multiple thermal cycles of PCR to denature template (and the resultant time loss needed for heating and cooling). Often, however, the template is repeatedly denatured, annealed, and extended with polymerase in the presence of ribonucleotide or deoxyribonucleotides under suitable reaction conditions.

Furthermore, whether the method generates a rolling circle intermediate or linear concatemers, an advantage of the method is that it requires a substantially reduced amount of primer (bivalent primer) as compared to conventional PCR, since following the initial cycle(s) an increasing percentage of the priming of nascent strand synthesis is primed from 3'-hydroxyl groups of the amplified strands, rather than from the oligonucleotide primer(s). In the case of a rolling circle intermediate, theoretically only a single bivalent primer molecule is necessary to generate the rolling circle which then can produce multiple concatenated copies by rolling circle-style polymerase catalysis using a polymerase capable of strand displacement of the lagging edge of the nascent strand as replication proceeds around the cyclized template.

In an embodiment, a product polynucleotide is assembled from a plurality of component polynucleotides by formation of overlapped strands of alternating polarity and having substantially complementary termini (see, FIG. 3). This method employs a series of overlapping substantially complementary termini to determine the linear order of component sequences in the final product. Concomitant with or subsequent to formation of the overlapped strands of the component polynucleotides in a reaction, a polynucleotide polymerase (e.g., a thermostable DNA polymerase) under suitable reaction conditions catalyzes strand elongation from the 3'-hydroxyl portions of the overlapped (annealed) joints, filling in the portion between joints and processively displacing or processively degrading exonucleolytically the 5' termini of downstream component strands of the same polarity as the nascent strand elongates. After a cycle of chain elongation forming substantially double-stranded polynucleotides, the reaction conditions are altered (typically by increasing the temperature) to effect denaturation of the double-stranded polynucleotides, followed by altering the reaction conditions to permit reannealing of complementary strands or portions thereof (i.e., overlapping termini) to form molecules having overlapped termini (joints), and chain elongation by a polynucleotide polymerase under suitable reaction conditions catalyzes strand elongation from the 3'-hydroxyl portions of the overlapped (annealed) joints, as in the first cycle. One to about 100 cycles of denaturation/annealing/polymerization can be performed to generate a product comprising the component polynucleotide sequences covalently linked in linear order according to the order of the overlapping joints. In this embodiment, a product polynucleotide can be constructed from a plurality of smaller component polynucleotides (typically oligonucleotides) and enables assembly of a variety of products with alternate substitutable polynucleotide components at a given position serving as structural "alleles" (see, FIG. 4). The component polynucleotides are often provided in single-strand form, but may initially be present in double-strand form and be denatured (typically by elevated temperature) for the assembly of the product by PCR amplification. Substantially any type of product polynucleotide can be assembled in this way, including cloning and expression vectors, viral genomes, gene therapy vectors, genes (including chimeric genes), polynucleotides encoding peptide libraries, protein libraries, vector libraries, viral libraries, and the like. In a variation, one or more of the component polynucleotides represents a site-directed mutation or variable-sequence kernel. In a variation, PCR employing a low-fidelity polymerase is used to introduce additional sequence variation into the product polynucleotide(s) during amplification cycles. The method can be used to produce a library of sequence-variant product polynucleotides, if desired.

In an embodiment of the invention, very long distance PCR is provided, wherein PCR or other suitable amplification method is used to generate, in a single reaction or in parallel reactions which are subsequently pooled, a set of overlapping large DNA fragments which can be denatured and annealed to form very large (e.g., greater than 25 to 50 kilobases) DNA structures composed of overlapped single strands of DNA having alternating polarity with each overlapped joint providing an extendable 3'-hydroxyl group for forming phosphodiester bonds catalyzed by a polynucleotide polymerase in the presence of free ribonucleotide or deoxyribonucleotides. Typically, the method comprises forming at least three overlapping polynucleotides, wherein the 3' terminus of a first single-stranded polynucleotide is substantially complementary to the 3' terminus of a second single-stranded polynucleotide of the opposite polarity, and wherein the 5' terminus of said second single-stranded polynucleotide is substantially complementary to the 3' terminus of a third single-stranded polynucleotide having polarity identical to said first single-stranded polynucleotide, thereby generating an overlapped structure capable of chain elongation by a suitable polymerase to generate a double-stranded product spanning the three initial overlapped polynucleotides. With such a method, polynucleotides of 50 kb to 100 kb or more can be generated by a facile amplification method capable of generating amplification products much longer than is possible with conventional long-range PCR methods. The method can comprise parallel processing PCR reactions, wherein a plurality of primer sets are employed in a single reaction or multiple reactions which are subsequently pooled, each primer sets priming the PCR amplification of a polynucleotide sequence which comprises terminal sequences which are complementary to terminal sequences in at least one other amplification product produced by a different primer set, thus generating a set of overlapping PCR products with which a large product spanning the entire set of PCR products is generated by end-complementary polymerase reaction.

In some embodiments of the invention, the polynucleotides product(s) generated thereby are labelled, such as with radioisotopic, biotinyl, or fluorescent label moieties, by incorporation of labelled ribonucleotide or deoxyribonucleotides or the like into nascent polynucleotide by polymerase-mediated catalysis.

The invention also provides kits comprising a bivalent primer polynucleotide and/or a plurality of component polynucleotides and instructions for use describing the present end-complementary amplification method disclosed herein. Frequently, a polynucleotide polymerase, such as a thermostable DNA polymerase (Taq or Vent™ polymerase) is also present in the kit. Optionally, one or more target polynucleotides may be provided in the kit, such as for calibration and/or for use as a positive control to verify correct performance of the kit.

In an embodiment, the invention provides a method termed continuous multiplex amplification which affords amplification of a plurality of initially unlinked polynucleotide species at substantially comparable amplification rates by forming a linked amplification product wherein the plurality of initially unlinked polynucleotide sequences are linked by end-complementary amplification. An amplification unit, termed an amplicon, comprising at least one copy of each member of the plurality of initially unlinked polynucleotide species is formed by one or more cycles of end-complementary amplification. From one to about 100, typically three to 35, amplification cycles can be conducted and result in formation of a population of linked amplification products, which can comprise concatemers of said amplicon. The amplification products can be linear or circular, as desired, based on appropriate selection of the bivalent primers. In a variation, the amplification product is cleaved with a nucleolytic agent, such as a restriction enzyme which cuts at least one restriction site present in the amplicon, DNase, nuclease S1, bleomycin, ionizing radiation, or the like or by other suitable cleaving means.

A further understanding of the nature and advantages of the invention will become apparent by reference to the remaining portions of the specification and drawings.

BRIEF DESCRIPTION OF THE DRAWINGS

FIGS. 1A and 1B Schematic of bivalent primer and concatemer formation in end-complementary PCR.

FIGS. 5A–E shows oligonucleotides used to construct the 2.7 kb circular plasmid P182Sfir by end-complementary polymerase reaction. In FIG. 5A, sequences R1 to R28 correspond to SEQ ID NOS: 3–30 respectively. In FIG. 5B, the sequences labeled 1–28 in the left hand column correspond to SEQ ID NOS:31–58 respectively. In FIG. 5C, sequences 58F to 44R correspond to SEQ ID NOS:59–82. In FIG. 5D, sequences 45R to 29R correspond to SEQ ID NOS:83–107. In FIG. 5E, sequences 29F to 57F correspond to SEQ ID NOS:108–136.

FIG. 8 Schematic for end-complementary polymerase reaction (ECPR) in conjunction with parallel-processing PCR to amplify very large polynucleotides, such as those larger than can be amplified reliably by conventional PCR using only a single primer set.

FIGS. 9A–9C Schematic of continuous circular multiplex amplification methodology exemplifying amplification of two unlinked polynucleotides, double-stranded ABC/A'B'C' and double-stranded DEF/D'E'F'. A and A', B and B', C and C', D and D', E and E', F and F' each represent a set of complementary (or substantially complementary) polynucleotide sequences present in the initially unlinked polynucleotides. X and X', Y and Y' each represent a set of complementary (or substantially complementary) polynucleotide sequences present in the bivalent primers CYD, C'X'D', FYA, and F'X'A'. In some embodiments, X and X' and/or Y and Y' can be omitted. FIG. 9A shows the initial (starting) conditions with a plurality of polynucleotide species (shown for example as two double-stranded molecules) to be amplified by continuous circular multiplex amplification. The second step, "Anneal with Primers", shows the structural features of the bivalent primers and their mode of annealing to single-stranded polynucleotide species, shown as denatured double-stranded complementary polynucleotides. The third step, "Extend and Melt", shows the amplification products after a cycle of extension primed by the bivalent primers; the amplification products are denatured for a subsequent round(s) of amplification. FIG. 9B shows the possible modes of reannealing of the amplification products generated from the first round of amplification. FIG. 9C shows the amplification products which can result from the second round (or subsequent rounds) of amplification; each of the product molecules is capable of self-replication as they have complementary ends, and they can also cross-replicate. Each of the product molecules comprises copies of the initially unlinked polynucleotide sequences in equimolar ratios.

FIGS. 10A–10C Schematic of continuous linear multiplex amplification methodology exemplifying amplification of two unlinked polynucleotides, double-stranded ABC/A'B'C' and double-stranded DEF/D'E'F'. A and A', B and B', C and C', D and D', E and E', F and F' each represent a set of complementary (or substantially complementary) polynucleotide sequences present in the initially unlinked polynucleotides. X and X', Y and Y' each represent a set of complementary (or substantially complementary) polynucleotide sequences. X' and Y are present in the bivalent primers CYD and C'X'D'. The univalent primers are F' and A. In some embodiments, X and X' and/or Y and Y' can be omitted. FIG. 10A shows the initial (starting) conditions with a plurality of polynucleotide species (shown for example as two double-stranded molecules) to be amplified by continuous circular multiplex amplification. The second step, "Anneal with Primers", shows the structural features of the bivalent and univalent primers and their mode of annealing to single-stranded polynucleotide species, shown as denatured double-stranded complementary polynucleotides. The third step, "Extend and Melt", shows the amplification products after a cycle of extension primed by the bivalent and univalent primers; the amplification products are denatured for a subsequent round(s) of amplification. FIG. 10B shows the possible modes of reannealing of the amplification products generated from the first round of amplification. FIG. 10C shows the amplification products which can result from the second round (or subsequent rounds) of amplification; each of the product molecules comprises copies of the initially unlinked polynucleotide sequences in equimolar ratios.

FIGS. 11A–11C Schematic of continuous circular multiplex amplification methodology exemplifying amplification of two possibly unlinked polynucleotides embedded in distinct locations in a genome or pool of DNA molecules. FIG. 11A shows the initial (starting) conditions with a plurality of polynucleotide sequences (shown for example as two double-stranded sequences embedded in discrete genomic locations) to be amplified by continuous circular multiplex amplification. First, the genomic sequences are amplified using a low concentration of conventional amplification primers (shown as PCR primers; C',F',A, and D) as indicated under "Anneal #1". The concentration of conventional primers, initial copy number, and number of amplification cycles is such that primers for rapidly extending fragments are consumed and slowly extending sequences are allowed to amplify. FIG. 11B shows that bivalent primers (FT3'XT7A and CYD) are used in subsequent rounds of amplification. In this example, one of the bivalent primers (FT3'XT7A) comprises the sequences for one or more promoter sequence, in this case a T3 promoter and a T7 promoter oriented in opposite transcriptional polarities. The mode of hybridization of the bivalent primers to denatured amplification product is shown under "Anneal with Primers", and the resultant amplification products are shown under "Extend and Melt". FIG. 11C shows possible modes of reannealing of the denatured products of amplification using the bivalent primers under "Reannealing". Examples of the resultant products of self-primed amplification are shown under "Extend". Each of the product polynucleotides shown have complementary ends and are capable of self-replication and cross-replication. The sequences X and Y, if present, can comprise restriction sites, if desired.

Figure 12:
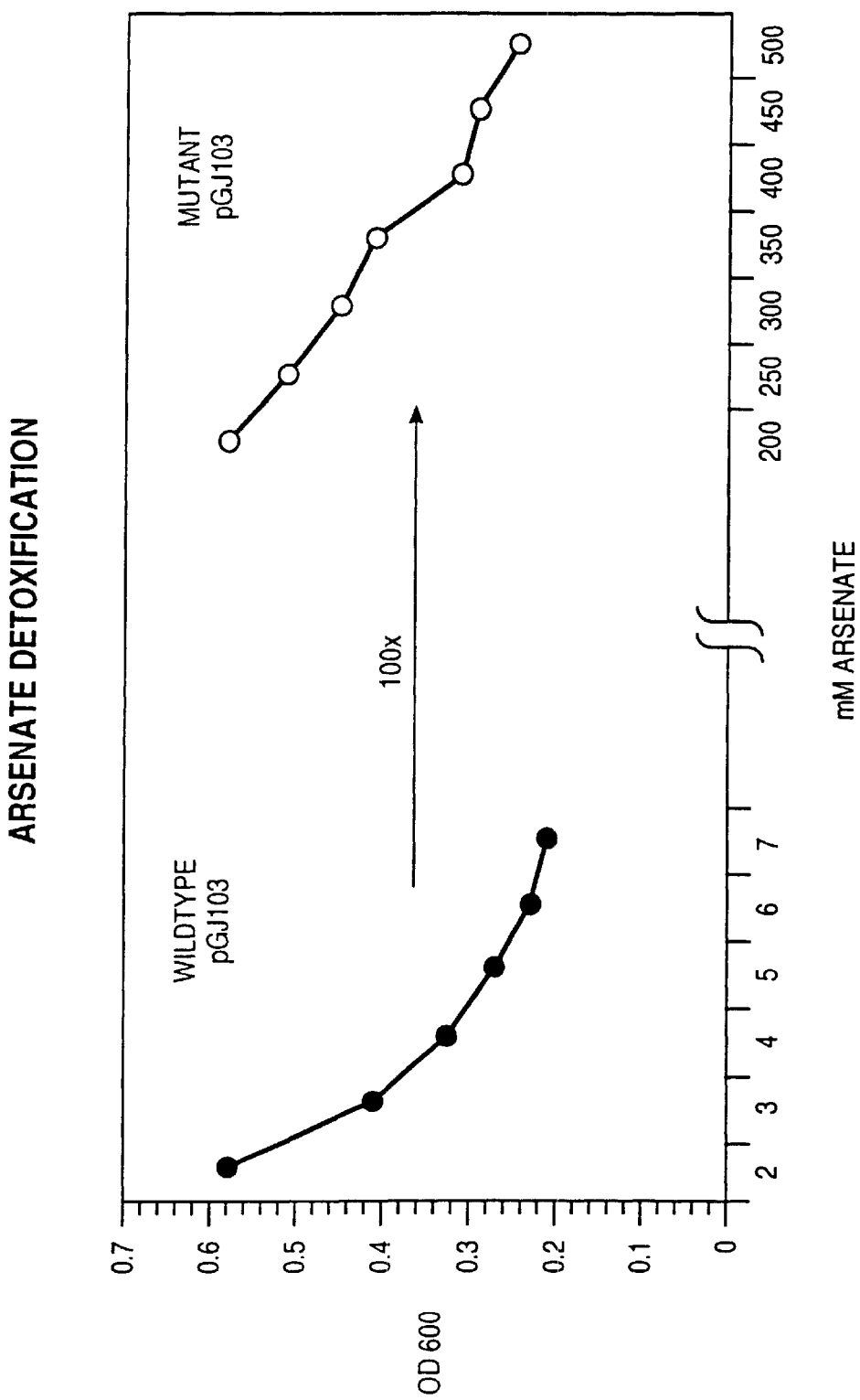
FIG. 12 Arsenate; arsenite and antimony resistance for *E. coli* strain TG1, without a plasmid, with plasmid pGJ103 with the wild type ars operon, or with pGJ103 mutagenized by three cycles of PCR shuffling. Cells grown overnight in LB with 2 mM, 10 mM or 128 mM arsenate were diluted 10,000-times into LB with added oxyanions as indicated and turbidity was measured after 16 hours growth at 37° C. Equal amounts of cells (OD600) were plated on plates with a range of arsenate concentrations and grown overnight at 37° C. Cell growth was quantitated by resuspending the cells and measuring the OD600.

FIG. 13 Cells as in FIG. 12 were washed and suspended in triethanol amine buffer and exposed to 3 mM $^{73}$As-arsenate. Samples were removed periodically, heated to 100° C., and centrifuged. $^{73}$As-arsenate and $^{73}$As-arsenite were quantitated after thin layer chromatographic separation.

DESCRIPTION OF THE PREFERRED EMBODIMENTS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

Definitions

Unless specified otherwise, the conventional notation used herein portrays polynucleotides as follows: the lefthand end of single-stranded polynucleotide sequences is the 5' end; the lefthand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the coding RNA transcript are referred to as "downstream sequences".

As used herein, the term "polynucleotide" refers to a polymer composed of a multiplicity of nucleotide units (ribonucleotide or deoxyribonucleotide or related structural variants) linked via phosphodiester bonds. A polynucleotide can be of substantially any length, typically from about 10 nucleotides to about 1×10$^9$ nucleotides or larger. As used herein, an "oligonucleotide" is defined as a polynucleotide of from 6 to 100 nucleotides in length. Thus, an oligonucleotide is a subset of polynucleotides.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. Generally, the term naturally-occurring refers to an object as present in a non-pathological (undiseased) individual, such as would be typical for the species.

The term "corresponds to" is used herein to mean that a polynucleotide sequence is homologous (i.e., is identical, not strictly evolutionarily related) to all or a portion of a reference polynucleotide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 12 nucleotides in length, frequently at least 15 to 18 nucleotides in length, and often at least 25 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 12 contiguous nucleotide positions wherein a polynucleotide sequence may be compared to a reference sequence of at least 12 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (1981) Adv. Appl. Math. 2: 482, by the homology alignment algorithm of Needleman and Wunsch (1970) J. Mol. Biol. 48: 443, by the search for similarity method of Pearson and Lipman (1988) Proc. Natl. Acad. Sci. (U.S.A.) 85: 2444, by computerized implementations of these algorithms (GAP, BESTFIT, FASTA, and TFASTA in the Wisconsin Genetics Software Package Release 7.0, Genetics Computer Group, 575 Science Dr., Madison, Wis.), or by inspection, and the best alignment (i.e., resulting in the highest percentage of homology over the comparison window) generated by the various methods is selected.

The term "sequence identity" means that two polynucleotide sequences are identical (i.e., on a nucleotide-by-nucleotide basis) over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison window of at least 20 nucleotide positions, frequently over a window of at least 25–50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

The primers herein are selected to be substantially complementary to the different strands of each specific sequence to be amplified. The primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, noncomplementary bases or longer sequences can be interspersed into the primer, provided that the primer sequence has sufficient complementarity with the sequence of the strand to be amplified to hybridize therewith and thereby form a template for synthesis of the extension product of the other primer.

As used herein, a "bivalent primer" is a polynucleotide having two regions of complementarity to a predetermined target polynucleotide: (1) a first portion which is in the 5' portion of the bivalent primer and which is substantially complementary to a sequence in the 5' portion of the sequence to be amplified (target sequence) in the target polynucleotide, and (2) a second portion which is in the 3' portion of the primer and which is substantially complementary to a sequence in the −3' portion of the sequence to be amplified (target sequence) in the target polynucleotide. The portion of the bivalent primer which is substantially complementary to a sequence in the 3' portion of the sequence to be amplified (target sequence) is sufficiently long and sufficiently complementary to the target sequence to anneal under the reaction conditions and serve as an extendable primer for the polymerase to catalyze chain elongation. Similarly, the portion of the bivalent primer which is substantially complementary to a sequence in the 5' portion of the sequence to be amplified (target sequence) is sufficiently long and sufficiently complementary to the target sequence to anneal under the reaction conditions and serve as an extendable primer for the polymerase to catalyze chain elongation. Practitioners in the art will select at their discretion the specific structure of the bivalent primer(s) to be used in view of the necessity for annealing to the target. Typically, the portions of the bivalent primer which is substantially complementary to a sequence in the 5' and 3' portions of the sequence to be amplified (target sequence) are each at least 12 to 15 nucleotides in length, often 18 to 20 nucleotides in length, and are preferably 100 percent identical to the complement of the annealing portion of the target sequence. Often, bivalent primers of the invention are oligonucleotides.

The term "primer" as used herein refers to an oligonucleotide whether occurring naturally as in a purified restriction digest or produced synthetically, which is capable of acting as a point of initiation of synthesis when placed under conditions in which synthesis of a primer extension product which is complementary to a nucleic acid strand is induced, i.e., in the presence of nucleotides and an agent for polymerization such as DNA polymerase and at a suitable temperature and pH. The primer is preferably single-stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the agent for polymerization. The exact lengths of the primers will depend on many factors, including temperature and source of primers. For example, depending on the complexity of the target sequence, the oligonucleotide primer typically contains 15–25 or more nucleotides, although it may contain fewer nucleotides. Short primer molecules generally require cooler temperatures to form sufficiently stable hybrid complexes with template. In some embodiments, the primers can be large polynucleotides, such as from about 200 nucleotides to several kilobases or more.

As used herein, "suitable reaction conditions" are those conditions suitable for conducting PCR amplification using conventional reagents. Such conditions are known or readily established by those of skill in the art, and can be exemplified by the reaction conditions used in U.S. Pat. Nos. 4,683,202, 4,683,195, and 4,800,159, which are incorporated herein by reference. As one example and not to limit the invention, suitable reaction conditions can comprise: 0.2 mM each dNTP, 2.2 mM $MgCl_2$, 50 mM KCl, 10 mM Tris-HCl pH 9.0, 0.1% Triton X-100.

As used herein the term "physiological conditions" refers to temperature, pH, ionic strength, viscosity, and like biochemical parameters which are compatible with a viable organism, and/or which typically exist intracellularly in a viable cultured yeast cell or mammalian cell. For example, the intracellular conditions in a yeast cell grown under typical laboratory culture conditions are physiological conditions. Suitable in vitro reaction conditions for PCR and many polynucleotide enzymatic reactions and manipulations are generally physiological conditions. In general, in vitro physiological conditions comprise 50–200 mM NaCl or KCl, pH 6.5–8.5, 20–45° C. and 0.001–10 mM divalent cation (e.g., $Mg^{++}$, $Ca^{++}$); preferably about 150 mM NaCl or KCl, pH 7.2–7.6, 5 mM divalent cation, and often include 0.01–1.0 percent nonspecific protein (e.g., BSA). A non-ionic detergent (Tween, NP-40 , Triton X-100) can often be present, usually at about 0.001 to 2%, typically 0.05–0.2% (v/v). Particular aqueous conditions may be selected by the practitioner according to conventional methods. For general guidance, the following buffered aqueous conditions may be applicable: 10–250 mM NaCl, 5–50 mM Tris HCl, pH 5–8, with optional addition of divalent cation(s) and/or metal chelators and/or nonionic detergents and/or membrane fractions and/or antifoam agents and/or scintillants.

As used herein, the terms "label" or "labeled" refers to incorporation of a detectable marker, e.g., by incorporation of a radiolabeled nucleotide or incorporation of nucleotide having biotinyl moieties that can be detected by marked avidin (e.g., streptavidin containing a fluorescent marker or enzymatic activity that can be detected by optical or calorimetric methods). Various methods of labeling polynucleotides are known in the art and may be used. Examples of labels include, but are not limited to, the following: radioisotopes (e.g., $^3H$, $^{14}C$, $^{35}S$, $^{125}I$ $^{131}I$), fluorescent labels (e.g., FITC, rhodamine, lanthanide phosphors), enzymatic labels (e.g., horseradish peroxidase, β-galactosidase, luciferase, alkaline phosphatase), biotinyl groups, and the like. In some embodiments, labels are attached by spacer arms of various lengths to reduce potential steric hindrance.

As used herein, "substantially pure" means an object species is the predominant species present (i.e., on a molar basis it is more abundant than any other individual macromolecular species in the composition), and preferably a substantially purified fraction is a composition wherein the object species comprises at least about 50 percent (on a molar basis) of all macromolecular species present.

Generally, a substantially pure composition will comprise more than about 80 to 90 percent of all macromolecular species present in the composition. Most preferably, the object species is purified to essential homogeneity (contaminant species cannot be detected in the composition by conventional detection methods) wherein the composition consists essentially of a single macromolecular species. Solvent species, small molecules (<500 Daltons), and elemental ion species are not considered macromolecular species.

The term "recombinant" used herein refers to macromolecules produced by recombinant DNA techniques wherein the gene coding for a polypeptide is cloned by known recombinant DNA technology. For example, an amplified or assembled product polynucleotide may be inserted into a suitable DNA vector, such as a bacterial plasmid, and the plasmid used to transform a suitable host. The gene is then expressed in the host to produce the recombinant protein. The transformed host may be prokaryotic or eukaryotic, including mammalian, yeast, Aspergillus and insect cells. One preferred embodiment employs bacterial cells as the host. Alternatively, the product polynucleotide may serve a non-coding function (e.g., promoter, origin of replication, ribosome-binding site, etc.).

Generally, the nomenclature used hereafter and many of the laboratory procedures in cell culture, molecular genetics, and nucleic acid chemistry and hybridization described below are those well known and commonly employed in the art. Standard techniques are used for recombinant nucleic acid methods, polynucleotide synthesis, in vitro polypeptide synthesis, and the like and microbial culture and transformation (e.g., electroporation). Generally enzymatic reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold spring Harbor, N.Y.; each of which is incorporated herein by reference) which are provided throughout this document. The procedures therein are believed to be well known in the art and are provided for the convenience of the reader. All the information contained therein is incorporated herein by reference.

Oligonucleotides can be synthesized on an Applied Bio Systems oligonucleotide synthesizer according to specifications provided by the manufacturer.

Methods for PCR amplification are described in the art (*PCR Technology: Principles and Applications for DNA Amplification* ed. HA Erlich, Stockton Press, New York, N.Y. (1989); *PCR Protocols: A Guide to Methods and Applications*, eds. Innis, Gelfland, Snisky, and White, Academic Press, San Diego, Calif. (1990); Mattila et al. (1991) *Nucleic Acids Res.* 19: 4967; Eckert, K. A. and Kunkel, T. A. (1991) *PCR Methods and Applications* 1: 17; and U.S. Pat. Nos. 4,683,202 and 4,965,188, each of which are incorporated herein by reference) and exemplified hereinbelow.

Overview

A basis of the present invention is the use of polymerase in combination with at least two polynucleotides having complementary ends which can anneal whereby at least one of said polynucleotides has a free 3'-hydroxyl capable of polynucleotide chain elongation by a DNA polymerase, such as a thermostable polymerase (e.g., *Thermus aquaticus* (Taq) polymerase or *Thermococcus litoralis* (Vent™) polymerase. In an embodiment, the method is performed using PCR, typically with multiple cycles of heat denaturation and DNA synthesis. However, there are several variations of the basic method of end-complementary polymerase reaction which are exemplified hereinbelow and which shall be evident to the skilled artisan in view of the present specification. Some variations do not require primers and/or sequential cycles of thermal denaturation.

In embodiments where the product size increases with the number of denaturation, annealing, and extension cycles (e.g., as the mean length of concatemers increase), it is typically advantageous to increase the denaturation temperature, and optionally increase the reannealing time, for subsequent cycles. Such conditions are readily optimized by the practitioner using pilot reactions to establish a calibration curve for any particular embodiment.

Single-Primer Amplification

A target polynucleotide is contacted with a bivalent primer typically comprising an oligonucleotide having two regions of complementarity to the target polynucleotide: (1) a first portion which is in the 5' portion of the primer and which is substantially complementary to a sequence in the 5' portion of the sequence to be amplified (target sequence) in the target polynucleotide, and (2) a second portion which is in the 3' portion of the primer and which is substantially complementary to a sequence in the 3' portion of the sequence to be amplified (target sequence) in the target polynucleotide. The contacting is performed under conditions suitable for hybridization of the bivalent primer to the target polynucleotide for polymerase-mediated chain elongation, most often following thermal denaturation of the target polynucleotide if it is initially present as a double-stranded form.

The first portion of the bivalent primer which is in the 5' portion of the primer and which is substantially complementary to a sequence in the 5' portion of the sequence to be amplified (target sequence) in the target polynucleotide is typically at least 12 nucleotides in length, often at least 15 nucleotides in length, frequently at least 18 nucleotides in length, and is commonly 20 to 25 or more nucleotides in length, but usually does not exceed 10,000 nucleotides in length and is frequently less than 50 to 500 nucleotides in length. The first portion of the bivalent primer is substantially identical to the complement of a sequence at the 5' end of the target sequence, however there may be additional terminal nucleotides of the first portion of the bivalent primer which are substantially non-identical to a target sequence or its complement. Such terminal nucleotides must be substantially non-interfering so that their presence does not significantly inhibit the capability of the bivalent primer to selectively anneal to the target sequence and initiate chain elongation under suitable reaction conditions in the presence of polymerase. Although the first portion of the bivalent primer is substantially identical to the complement of a sequence at the a 5' end of the target sequence, it need not be exactly identical; often a sequence identity of at least 80 percent is sufficient, typically at least 90 percent sequence identity is present, and preferably at least 95 percent or 100 percent sequence identity is present. As the length of the complementary sequence increases, typically the percentage of sequence identity necessary for specific annealing decreases within certain limits (pp. 399–407, in Berger and Kimmel, *Methods in Enzymology*, Volume 152. *Guide to Molecular Cloning Techniques* (1987), Academic Press, Inc., San Diego, Calif., which is incorporated herein by reference).

The second portion of the bivalent primer which is in the 3' portion of the primer and which is substantially complementary to a sequence in the 3' portion of the sequence to be amplified (target sequence) in the target polynucleotide is typically at least 12 nucleotides in length, often at least 15 nucleotides in length, frequently at least 18 nucleotides in length, and is commonly 20 to 25 or more nucleotides in length, but usually does not exceed 10,000 nucleotides in length and is frequently less than 50 to 500 nucleotides in length. The second portion of the bivalent primer is substantially identical to the complement of a sequence at the 3' end of the target sequence, however there may be additional terminal nucleotides of the first portion of the bivalent primer which are substantially non-identical to a target sequence or its complement. Such terminal nucleotides must be substantially non-interfering so that their presence does not significantly inhibit the capability of the bivalent primer to selectively anneal to the target sequence and initiate chain elongation under suitable reaction conditions in the presence of polymerase. Although the second portion of the bivalent primer is substantially identical to the complement of a sequence at the 3' end of the target sequence, it need not be exactly identical; often a sequence identity of at least 80 percent is sufficient, typically at least 90 percent sequence identity is present, and preferably at least 95 percent or 100 percent sequence identity is present. In some embodiments, sequence identity of less than 80 percent is practicable, but the amount of sequence identity and length of overlap for the joints is determined by the discretion of the practitioner.

The amount of sequence identity necessary for any given application will vary depending on several factors including: (1) complexity of the population of polynucleotides in which the target polynucleotide(s) is/are present, (2) temperature and ionic strength, (3) sequence composition of the target sequence, (4) length of sequence identity, and (5) size of the primer. Practitioners will select bivalent primers having a first portion with sufficient sequence identity and length to serve as selective amplification primers which specifically hybridize to the desired target polynucleotide(s). Specific hybridization is the formation of hybrids between a primer polynucleotide and a target polynucleotide, wherein the primer polynucleotide preferentially hybridizes to the target DNA such that, for example, at least one discrete band can be identified on a gel of amplification products obtained from amplification of genomic DNA prepared from eukaryotic cells that contain (or are spiked with) the target polynucleotide sequence. In some instances, a target sequence may be present in more than one target polynucleotide species (e.g., a particular target sequence may occur in multiple members of a gene family or in a known repetitive sequence). It is evident that optimal hybridization conditions will vary depending upon the sequence composition and length(s) of the targeting polynucleotide(s) and target(s), and the experimental method selected by the practitioner. Various guidelines may be used to select appropriate primer sequences and hybridization conditions (see, Maniatis et al., *Molecular Cloning: A Laboratory Manual* (1989), 2nd Ed., Cold Spring Harbor, N.Y.; Berger and Kimmel, *Methods in Enzymology*. Volume 152. *Guide to Molecular Cloning Techniques* (1987), Academic Press, Inc., San Diego, Calif.; *PCR Protocols: A Guide to Methods and Applications*, eds. Innis, Gelfland, Snisky, and White, Academic Press, San Diego, Calif. (1990); Benton W D and Davis R W (1977) *Science* 196: 180; Goodspeed et al. (1989) *Gene* 76: 1; Dunn et al. (1989) *J. Biol. Chem.* 264: 13057 which are incorporated herein by reference.

The target polynucleotide may be substantially homogeneous or may be present in a mixture of polynucleotide species (e.g., in a genome, biological sample, or mixture of synthetic polynucleotides). Subsequent or concomitant with the contacting of the bivalent primer to the target polynucleotide, a polynucleotide polymerase, such as a thermostable DNA polymerase, e.g., Taq polymerase, TThI polymerase (Perkin Elmer) or Vent™ (New England Biolabs, Beverly, Mass.), catalyzes, under suitable reaction conditions, polynucleotide synthesis (chain elongation) primed from the 3'-hydroxyl of the annealed bivalent primer to form a strand complementary to the target sequence, thereby forming a nascent complementary strand. Following completion of the nascent complementary strand spanning the target sequence, the target polynucleotide and the nascent strand are denatured, typically by elevation of temperature, and allowed to reanneal, typically by reduction of temperature, with another molecule of the bivalent primer species or with a complementary strand of a target polynucleotide or an amplified copy thereof. The denatured nascent strand species following the first elongation cycle will contain a copy of the target sequence and has a terminal repeat of its 5'-terminal sequence at the 3' terminus, resulting from the bivalent primer, and wherein the terminal repeat is of sufficient length to support annealing under PCR conditions to an overlapping complementary strand in a head-to-tail arrangement (see, FIG. 1). Following reannealing, the described polymerase elongation/denaturation/reannealing cycle is repeated from 1 to about 100 times as desired, resulting in formation of amplified product which comprises head-to-tail concatemers of the target sequence. The concatemers typically increase in length as the number of amplification cycles increase and as the amount of bivalent primer decreases. Following amplification forming concatameric head-to-tail repeats of the target sequence, the concatemer(s) can optionally be resolved, such as (1) by cleaving with a restriction endonuclease which cuts-within (or at the termini of) the concatemeric unit(s), (2) by homologous recombination between concatemer units to form covalently closed circles, or (3) by cleavage with a restriction endonuclease followed by ligation with DNA ligase to form covalently closed circles and/or by direct transformation into host cells for in vivo ligation.

By this method, a single primer (bivalent primer) is used to amplify a target polynucleotide sequence having a predetermined 5' terminal sequence and a predetermined 3' terminal sequence. The predetermined 5' terminal sequence and a predetermined 3' terminal sequence may be contained internally within a larger polynucleotide; hence the use of the term "terminal" refers only to their terminality within the target sequence, not necessarily the complete target polynucleotide which may be a superset of the target sequence.

Rolling Circle PCR Amplification

Figure 2:
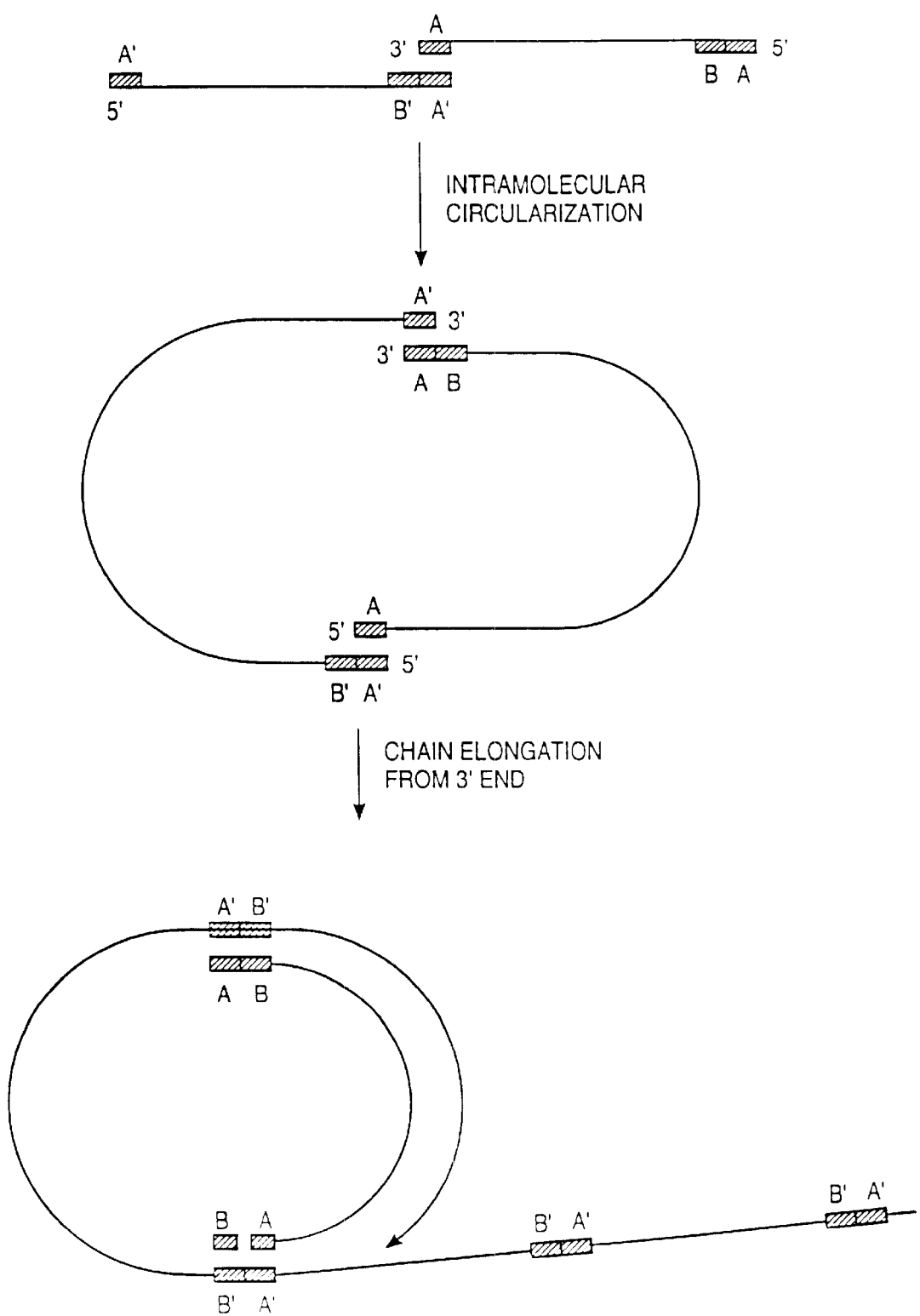
FIG. 2 Schematic depiction of cyclized intermediates and rolling circle amplification.

Often, a target polynucleotide sequence which is amplified by the present method will form amplification intermediates in the form of cyclized DNA (see, FIG. 2), as a result of the 3' terminus of an overlapped nascent strand annealing to the 3' terminus of an overlapped complementary strand forming a cyclized (circular) structure similar to a gapped circle. The cyclized structure has a strand with an extendable 3'-hydroxyl which can be extended with a DNA polymerase substantially lacking exonuclease activity (e.g., a thermostable polymerase such as Vent(exo$^-$)™ or Klenow fragment, etc.) in a rolling circle format whereby the leading terminus of the nascent strand continually displaces the lagging portion of the nascent strand (see, FIG. 2) producing a concatemeric single strand propagating from the rolling circle intermediate. Most often, such rolling circle intermediates will form under dilute conditions more favorable to intramolecular cyclization of overlapped strands than to formation of additional intermolecular overlaps. Once a rolling circle intermediate is established, the template need not be denatured in order to continue amplification of the target sequence as in conventional PCR, since the polymerase continues around the circle processively. Thus, the advantageous formation of the rolling circle intermediate in the present method avoids the necessity of multiple thermal cycles of PCR to repeatedly denature and renature the amplification template (and the resultant time loss needed for heating and cooling).

Overlapped Assembly of Polynucleotides

The present invention also provides for assembly of one or more product polynucleotide(s) from a plurality of component polynucleotides which have overlapping complementary sequence portions at their termini. The component polynucleotides are conveniently single-stranded oligonucleotides, but can include double-stranded polynucleotides (which are generally denatured with elevated temperature) and long single-stranded polynucleotides.

Figure 3:
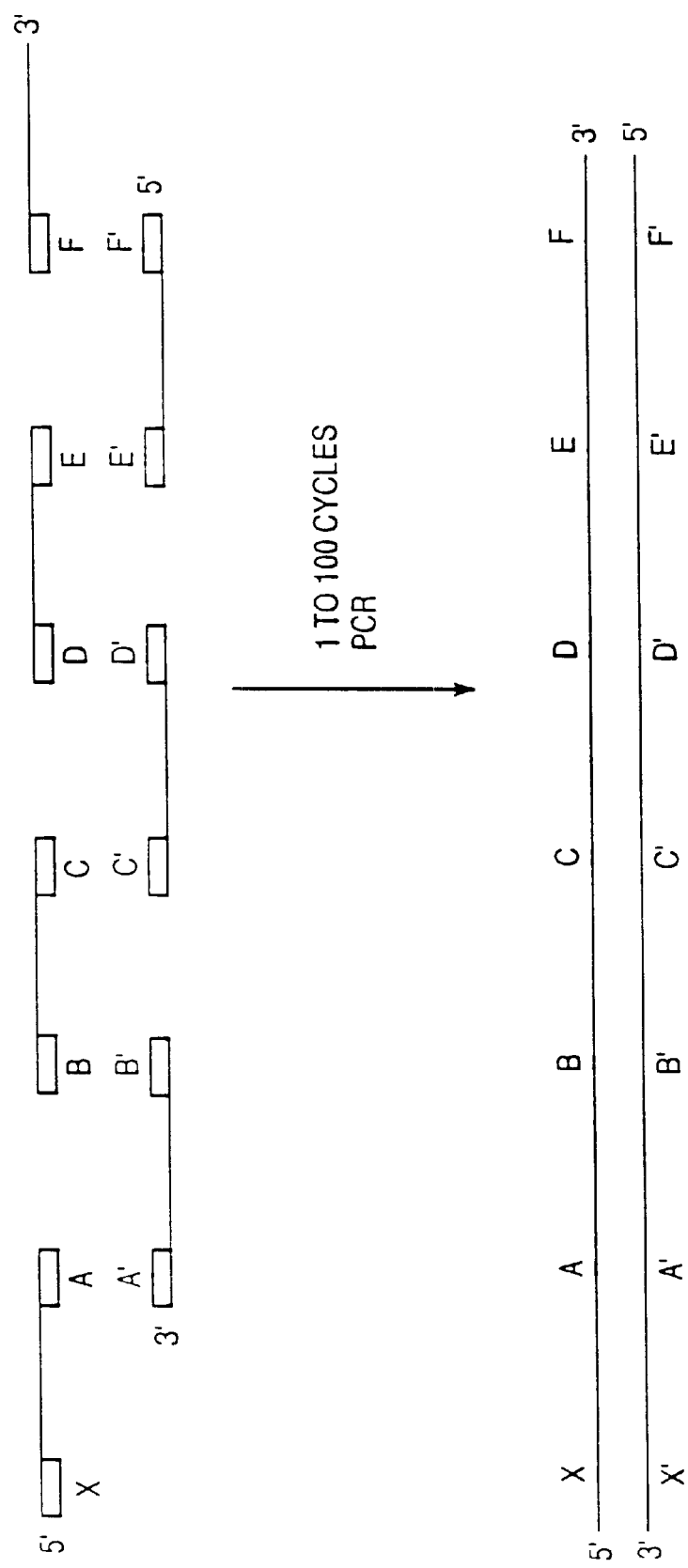
FIG. 3 Schematic of overlapping fragment PCR for construction and amplification of larger products from component polynucleotides.
Figure 4:
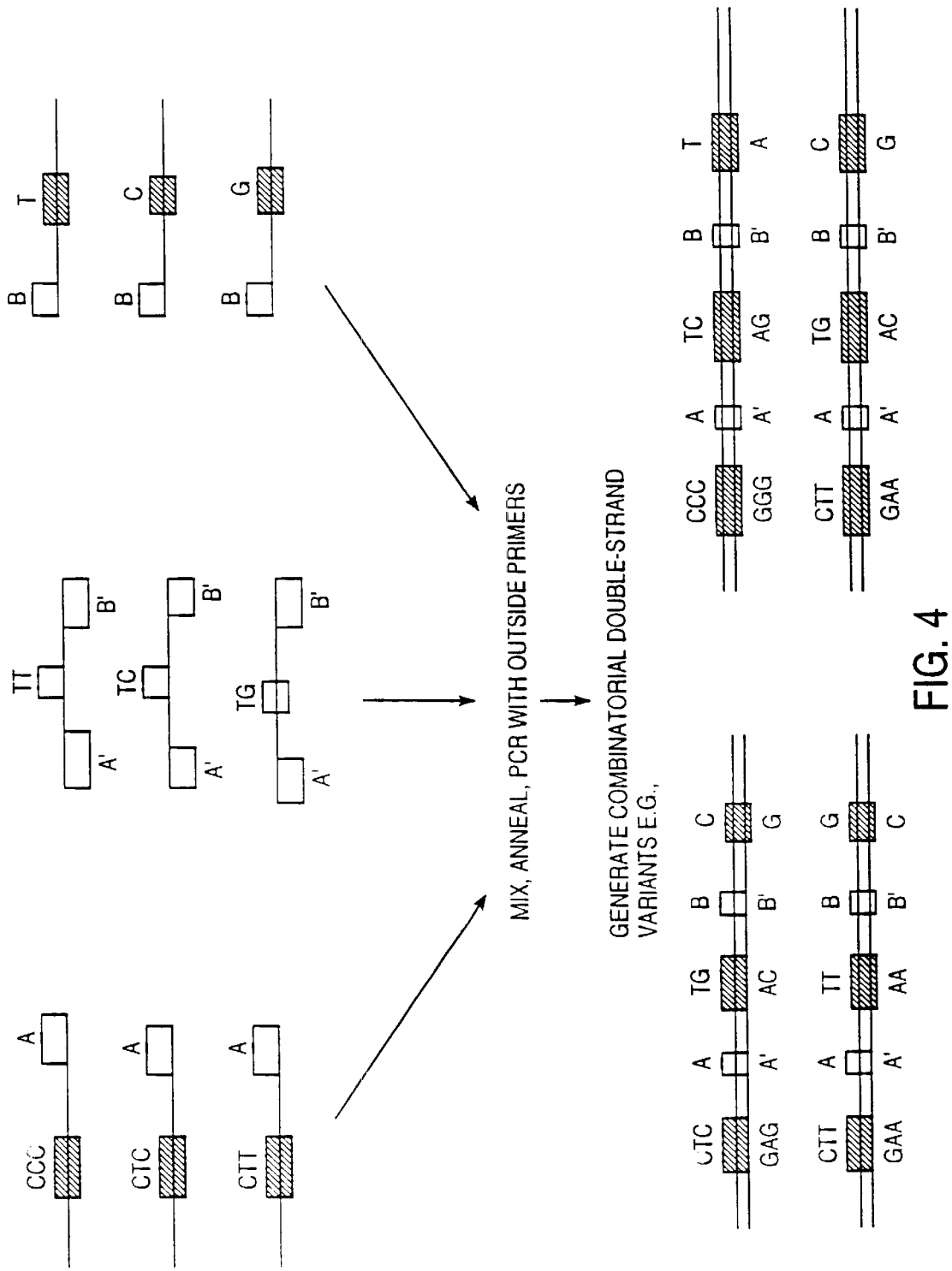
FIG. 4 Schematic of multiple "alleles" with overlapping fragment PCR.

A desired product polynucleotide (or polynucleotide library) is assembled from a plurality of component polynucleotides by formation of overlapped strands of alternating polarity and having substantially complementary termini (see, FIG. 3). This method employs a series of overlapping substantially complementary termini to determine the linear order of component sequences in the final product. Concomitant with or subsequent to formation of the overlapped strands of the component polynucleotides in a reaction, a polynucleotide polymerase (e.g., a thermostable DNA polymerase) under suitable reaction conditions catalyzes strand elongation from the 3'-hydroxyl portions of the overlapped (annealed) joints, filling in the portion between joints and processively displacing or processively degrading exonucleolytically the 5' termini of downstream component strands of the same polarity as the nascent strand elongates. After a cycle of chain elongation forming substantially double-stranded polynucleotides, the reaction conditions are altered (typically by increasing the temperature) to effect denaturation of the double-stranded polynucleotides, followed by altering the reaction conditions to permit reannealing of complementary strands or portions thereof (i.e., overlapping termini) to form molecules having overlapped termini (joints), and chain elongation by a polynucleotide polymerase under suitable reaction conditions catalyzes strand elongation from the 3'-hydroxyl portions of the overlapped (annealed) joints, as in the first cycle. One to about 100 cycles of denaturation/annealing/polymerization can be performed to generate a product comprising the component polynucleotide sequences covalently linked in linear order according to the order of the overlapping joints. In this embodiment, a product polynucleotide can be constructed from a plurality of smaller component polynucleotides (typically oligonucleotides) and enables assembly of a variety of products with alternate substitutable polynucleotide components at a given position serving as structural "alleles" (see, FIG. 4). The component polynucleotides are often provided in single-strand form, but may initially be present in double-strand form and be denatured (typically by elevated temperature) for the assembly of the product by PCR amplification. Substantially any type of product polynucleotide can be assembled in this way, including cloning and expression vectors, viral genomes, gene therapy vectors, genes (including chimeric genes), polynucleotides encoding peptide libraries, and the like. In a variation, one or more of the component polynucleotides represents a site-directed mutation or variable-sequence kernal. In a variation, PCR employing a low-fidelity polymerase is used to introduce additional sequence variation into the product polynucleotide(s) during amplification cycles. The method can be used to produce a library of sequence-variant product polynucleotides, if desired.

Kits

The invention also provides kits comprising a bivalent primer polynucleotide and/or a plurality of component polynucleotides and instructions for use describing the present end-complementary amplification method disclosed herein. Frequently, a polynucleotide polymerase, such as a thermostable DNA polymerase (Taq or Vent™ polymerase) is also present in the kit. Optionally, one or more target polynucleotides may be provided in the kit, such as for calibration and/or for use as a positive control to verify correct performance of the kit.

General Aspects

The target polynucleotides or component polynucleotides may be obtained from any source, for example, from plasmids such as pBR322, from cloned DNA or RNA, or from natural DNA or RNA from any source, including bacteria, yeast, viruses, and higher organisms such as plants or animals. DNA or RNA may be extracted from blood, tissue material such as chorionic villi or amniotic cells by a variety of techniques such as that described by Maniatis et al., Molecular Cloning: A Laboratory Manual, (New York: Cold Spring Harbor Laboratory, 1982), pp. 280–281. Alternatively, the polynucleotides may be produced by chemical synthesis by any of the art-recognized methods.

Any specific nucleic acid sequence can be produced by the present process. It is only necessary that a sufficient number of bases at both ends of the sequence be known in sufficient detail so that a bivalent primers can be prepared which will hybridize to the desired sequence and at relative positions along the sequence such that an extension product initially synthesized from the bivalent primer, when it is separated from its template (complement), can anneal with a stand of the opposite polarity to form an overlapped joint of a head-to-tail concatemer and serve as a template for extension of the 3'-hydroxyl from each overlapped joint. The greater the knowledge about the bases at both ends of the sequence, the greater can be the specificity of the primer for the target nucleic acid sequence, and thus the greater the efficiency of the process. It will be understood that the word bivalent primer as used hereinafter may refer to more than one bivalent primer, particularly in the case where there is some ambiguity in the information regarding the terminal sequence(s) of the fragment to be amplified. For instance, in the case where a nucleic acid sequence is inferred from protein sequence information a collection of primers containing sequences representing all possible codon variations based on degeneracy of the genetic code will be used for each strand.

The polynucleotide primers may be prepared using any suitable method, such as, for example, the phosphotriester and phosphodiester methods, or automated embodiments thereof. In one such automated embodiment diethylphosphoramidites are used as starting materials and may be synthesized as described by Beaucage et al. (1981) Tetrahedron Letters 22: 1859. One method for synthesizing oligonucleotides on a modified solid support is described in U.S. Pat. No. 4,458,066. It is also possible to use a primer which has been isolated from a biological source (such as a restriction endonuclease digest or the like).

The specific nucleic acid sequence is produced by using the target polynucleotide containing that sequence as a template. If the target polynucleotide contains two strands, it is necessary to separate the strands of the nucleic acid before it can be used as the template, either as a separate step or simultaneously with the synthesis of the primer extension products. This strand separation can be accomplished by any suitable denaturing method including physical, chemical or enzymatic means. One physical method of separating the strands of the polynucleotide involves heating the polynucleotide until it is substantially denatured. Typical heat denaturation may involve temperatures ranging from about 80° to 105° C. for times ranging from about 10 seconds to about 10 minutes or more. Strand separation may also be induced by an enzyme from the class of enzymes known as helicases or the enzyme RecA, which has helicase activity and in the presence of rATP is known to denature DNA. The reaction conditions suitable for separating the strands of polynucleotides with helicases are described by Cold Spring Harbor Symposia on Quantitative Biology, Vol. XLIII "DNA: Replication and Recombination" (New York: Cold Spring Harbor Laboratory, 1978), B. Kuhn et al., "DNA Helicases", pp. 63–67, and techniques for using RecA are reviewed in C. Radding, Ann. Rev. Genetics, 16:405–37 (1982).

PCR synthesis can be performed using any suitable method. Generally it occurs in a buffered aqueous solution, preferably at a pH of 7–9, most preferably about 8. The bivalent primer(s) is/are added in suitable amounts (molar ratio to target), typically less than conventional PCR methods because of the self-priming nature of the overlapped concatemers. The deoxyribonucleoside triphosphates DATP, dCTP, dGTP and TTP are also added to the synthesis mixture in adequate amounts and the resulting solution is heated to about 85°–100° C. for from about 1 to 10 minutes, preferably from 1 to 4 minutes. After this heating period the solution is allowed to cool to from 20°–40° C., which is preferable for the primer hybridization. To the cooled mixture is added an agent for polymerization, and the reaction is allowed to occur under conditions known in the art. This synthesis reaction may occur at from room temperature up to a temperature above which the agent for polymerization no longer functions efficiently. Thus, for example, if DNA polymerase is used as the agent for polymerization, the temperature is generally no greater than about 45° C. The agent for polymerization may be any compound or system which will function to accomplish the synthesis of primer extension products, including enzymes. Suitable enzymes for this purpose include, for example, $E.$ $coli$ DNA polymerase I, Klenow fragment of $E.$ $coli$ DNA polymerase I, T4 DNA polymerase, other available DNA polymerases, reverse transcriptase, and other enzymes, including heat-stable enzymes, which will facilitate combination of the nucleotides in the proper manner to form the primer extension products which are complementary to each nucleic acid strand. Generally, the synthesis will be initiated at the 3' end of the primer and proceed in the 5' direction along the template strand, until synthesis terminates, producing molecules of different lengths.

The newly synthesized strand and its complementary nucleic acid strand form a double-stranded molecule which is used in the succeeding steps of the process. In the next step, the strands of the double-stranded molecule are separated using any of the procedures described above to provide single-stranded molecules.

The steps of strand separation and extension product synthesis can be repeated as often as needed to produce the desired quantity of the specific nucleic acid sequence. The amount of the specific nucleic acid sequence produced will accumulate in an exponential fashion and the average size of the product will also increase as the length of the concatemers increases with each cycle.

The method herein may also be used to enable detection and/or characterization of specific nucleic acid sequences associated with infectious diseases, genetic disorders or cellular disorders such as cancer, e.g., oncogenes. Amplification is useful when the amount of nucleic acid available for analysis is very small, as, for example, in the prenatal diagnosis of sickle cell anemia using DNA obtained from fetal cells.

Continuous Multiplex Amplification

Figure 9C:
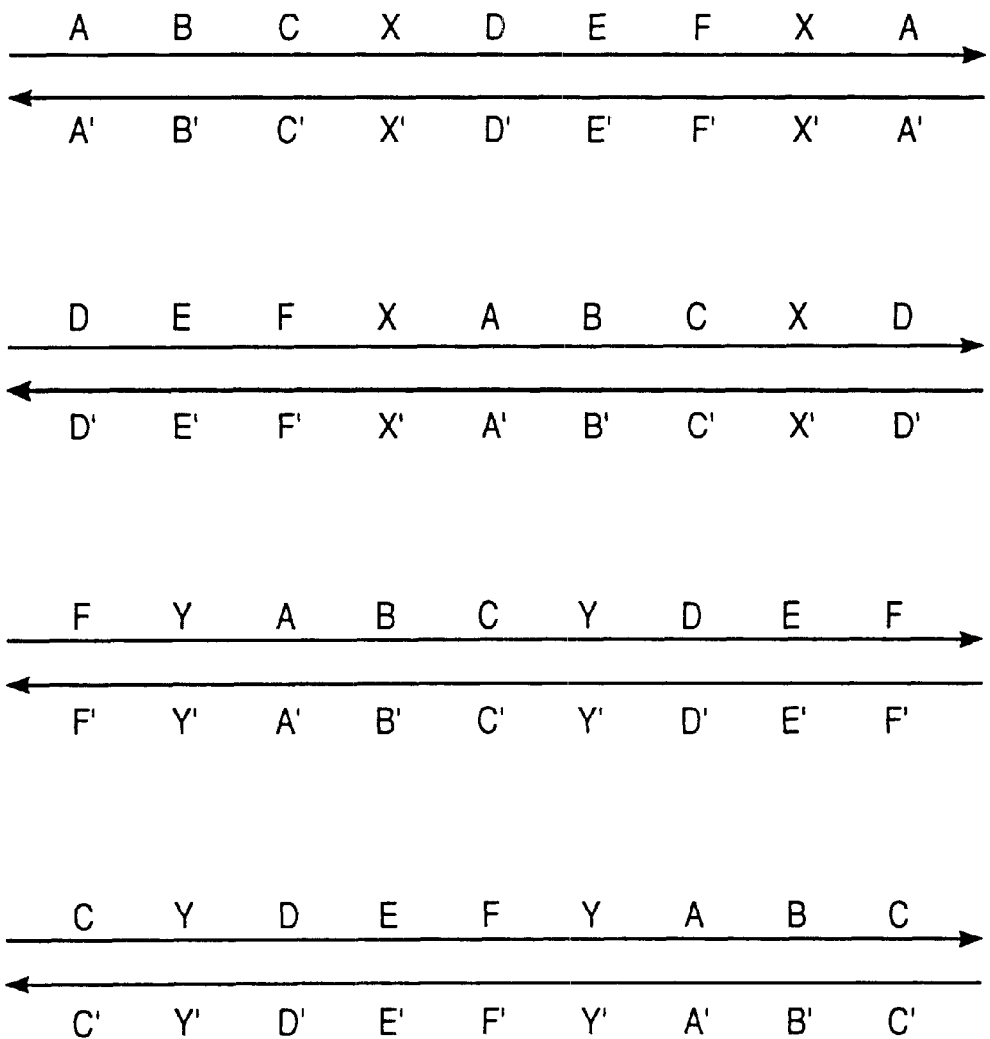
Figure 10B:
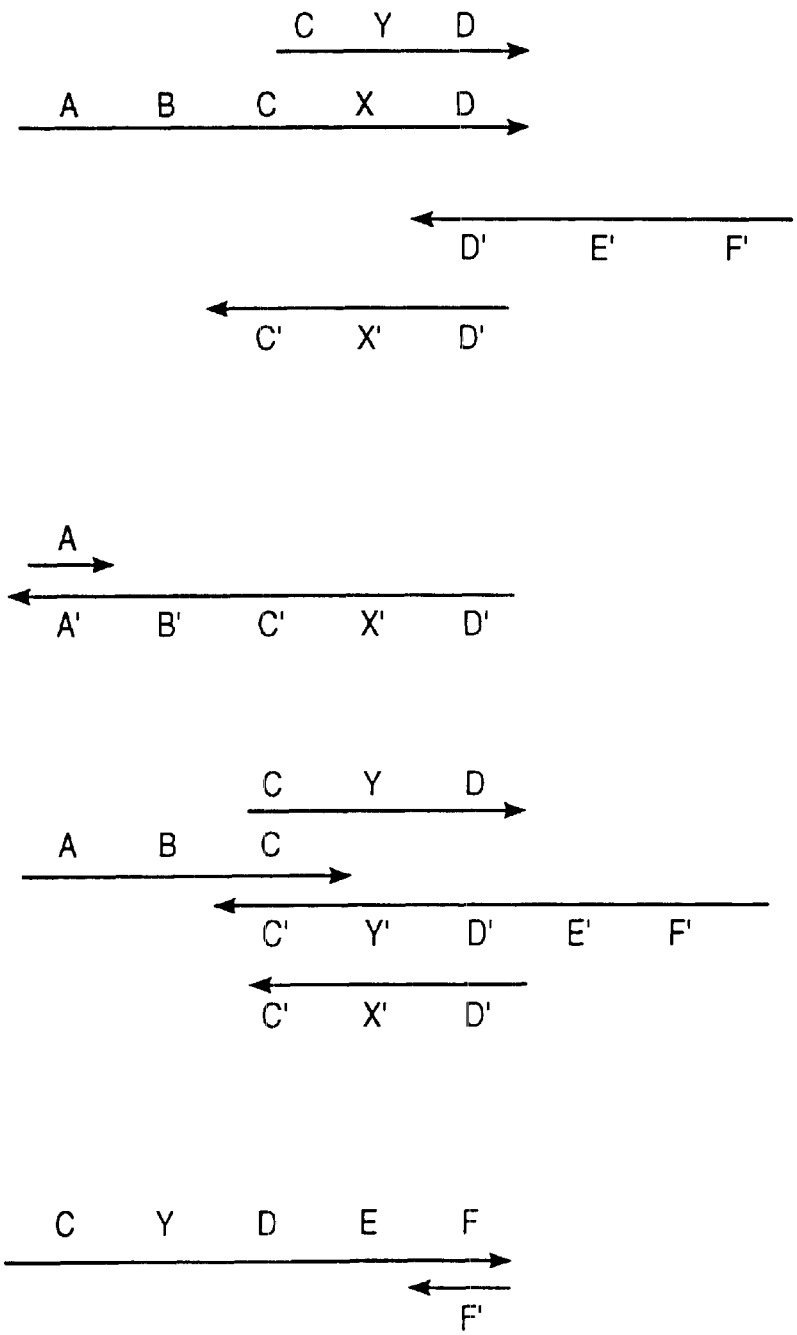

Continuous multiplex amplification can be used to amplify by any suitable amplification method, typically by PCR, a plurality of unlinked or distantly linked polynucleotide sequences. Certain genetic diagnostic tests required amplification of multiple segments (e.g., exons) of a gene. Each segment is typically amplified in a separate amplification reaction. Unfortunately , it is generally difficult or impossible to amplify each segment in approximately equimolar ratios due to differences in priming efficiency, length of extension, secondary structure, or other factors which affect amplification rate. In continuous multiplex amplification, the amplification reactions can be run together in a single reaction vessel using a common pool of reagents where the unlinked (or distantly linked) sequences become part of the same amplification product, which affords the substantially equimolar amplification of the unlinked (or distantly linked) sequences. An embodiment of the invention is illustrated schematically in FIGS. 9A–9C in the case of amplifying two unlinked sequences represented in the double-standard polynucleotide fragments ABC/A'B'C' and DEF/D'E'F' primers C'X'D', F'X'A, FYA, and CYD are added and annealed to the denatured polynucleotide fragments; the primer concentrations are typically lower than conventionally used for PCR primers. X and Y, and their complements X' and Y' are generally predetermined sequences which are selected to destabilize the primer:primer hybrids CYD/C'Y'D' and FYA/F'Y'A', such as by having the X and Y sequences (and their complements) lack substantial sequence identity. After extension with a polymerase, the following products and their complements result: ABCXD, DEFXA, FYABC, and CYDEF. A variety of hybrid combinations of product:product and primer:product can form and after another round of amplification a variety of amplification products result. Each of the pairs is capable of self-priming with its complement or with the complement of another fragment which has a complementary sequence. Through multiple cycles of amplification, the initial primer population becomes depleted and primarily extended products remain. These extended products will prime each other and generate increasingly longer amplification products which contain the initial unlinked (or distantly linked) sequences in equal amounts. After completion of amplification, several options can be pursued; the amplification product(s) can be used directly, the x and/or Y sequences can contain restriction sites (preferably unique site) to allow digestion with the restrictino enzyme and, if desired, separation and/or purification of the two (or more) originally unlinked sequences. Alternatively, or in combination, transcription promoters (e.g., T3 and T7) can be included in X and/or Y sequences to facilitate transcription of the amplified sequences. FIGS. 10A–10C show a linear format of the continuous multiplex amplification method. FIGS. 11A–11C show an embodiment of circular continuous multiplex amplification wherein bivalent primers contain T3 and T7 promoters and the functional promoter sequences are thereby introduced into the amplification product(s)

The following examples are given to illustrate the invention, but are not to be limiting thereof.

EXPERIMENTAL EXAMPLES

The following examples are offered by way of example and not by way of limitation. Variations and alternate embodiments will be apparent to those of skill in the art.

Example 1
LacZ Alpha Gene Reassembly

This example shows that small fragments having overlapping regions of homology can be amplified and reassembled by PCR amplification methods in the absence of any primer.

1) Substrate Preparation

The substrate for the reassembly reaction was the dsDNA polymerase chain reaction ("PCR") product of the wild-type LacZ alpha gene from pUC18. (Gene Bank No. XO2514) The primer sequences were 5'AAAGCGTCGATTTTTGT-GAT3' (SEQ ID NO:1) and 5'ATGGGGTTCCGCGCA-CATTT3' (SEQ ID NO:2). The free primers were removed from the PCR product by Wizard PCR prep (Promega, Madison Wis.) according to the manufacturer's directions. The removal of the free primers was found to be important.

2) DNAseI Digestion

About 5 μg of the DNA substrate was digested with 0.15 units of DNAseI (Sigma, St. Louis Mo.) in 100 μl of (50 mM Tris-HCl pH 7.4, 1 mM $MgCl_2$), for 10–20 minutes at room temperature. The digested DNA was run on a 2% low melting point agarose gel. Fragments of 10–70 basepairs (bp) were purified from the 2% low melting point agarose gels by electrophoresis onto DE81 ion exchange paper (Whatman, Hillsborough Oreg.). The DNA fragments were eluted from the paper with 1 M NaCl and ethanol precipitated.

3) DNA Reassembly

The purified fragments were resuspended at a concentration of 10–30 ng/μl in PCR Mix (0.2 mM each dNTP, 2.2 mM $MgCl_2$, 50 mM KCl, 10 mM Tris-HCl pH 9.0, 0.1% Triton X-100, 0.3 μl Taq DNA polymerase, 50 μl total volume). No primers were added at this point. A reassembly program of 94° C. for 60 seconds, 30–45 cycles of [94° C. for 30 seconds, 50–55° C. for 30 seconds, 72° C. for 30 seconds] and 5 minutes at 72° C. was used in an M J Research (Watertown Mass.) PTC-150 thermocycler. The PCR reassembly of small fragments into larger sequences was followed by taking samples of the reaction after 25, 30, 35, 40, and 45 cycles of reassembly.

Whereas the reassembly of 100–200 bp fragments can yield a single PCR product of the correct size, 10–50 base fragments typically yield some product of the correct size, as well as products of heterogeneous molecular weights. Most of this size heterogeneity appears to be due to single-stranded sequences at the ends of the products, since after restriction enzyme digestion a single band of the correct size is obtained.

4) PCR With Primers

After dilution of the reassembly product into the PCR Mix with 0.8 μM of each of the above primers (SEQ ID Nos: 1 and 2) and about 15 cycles of PCR, each cycle consisting of (94° C. for 30 seconds, 50° C. for 30 seconds and 72° C. for 30 seconds), a single product of the correct size was obtained.

5) Cloning and Analysis

The PCR product from step 4 above was digested with the terminal restriction enzymes BamHI and EcoO109 and gel purified as described above in step 2. The reassembled fragments were ligated into pUC18 digested with BamHI and EcoO109. E. coli were transformed with the ligation mixture under standard conditions as recommended by the manufacturer (Stratagene, San Diego Calif.) and plated on agar plates having 100 μg/ml ampicillin, 0.004% X-gal and 2 mM IPTG. The resulting colonies having the HinDIII-NheI fragment which is diagnostic for the ++ recombinant were identified because they appeared blue.

This Example illustrates that a 1.0 kb sequence carrying the LacZ alpha gene can be digested into 10–70 bp fragments, and that these gel purified 10–70 bp fragments can be reassembled to a single product of the correct size, such that 84% (N=377) of the resulting colonies are $LacZ^+$ (versus 94% without shuffling). This principal finding is extended substantially in the present invention to assemble component polynucleotides into product polynucleotides, and the component polynucleotides are not limited to randomly digested fragments of a naturally-occurring gene sequence.

The DNA encoding the LacZ gene from the resulting $LacZ^-$ colonies was sequenced with a sequencing kit (United States Biochemical Co., Cleveland Ohio) according to the manufacturer's instructions and the genes were found to have point mutations due to the reassembly process (Table 1). 11/12 types of substitutions were found, and no frame-shifts.

TABLE 1

Mutations introduced by mutapenic shuffling

| Transitions | Frequency | Transversions | Frequency |
|---|---|---|---|
| G - A | 6 | A - T | 1 |
| A - G | 4 | A - C | 2 |
| C - T | 7 | C - A | 1 |
| T - C | 3 | C - G | 0 |
|  |  | G - C | 3 |
|  |  | G - T | 2 |
|  |  | T - A | 1 |
|  |  | T - G | 2 |

A total of 4,437 bases of shuffled lacZ DNA were sequenced.

The rate of point mutagenesis during DNA reassembly from 10–70 bp pieces was determined from DNA sequencing to be 0.7% (N=4,473), which is similar to error-prone PCR. Without being limited to any theory it is believed that the rate of point mutagenesis may be lower if larger fragments are used for the reassembly, or if a proofreading polymerase is added.

When plasmid DNA from 14 of these point-mutated $LacZ^-$ colonies were combined and again reassembled/shuffled by the method described above, 34% (N=291) of the resulting colonies were $LacZ^+$, and these colonies presumably arose by recombination of the DNA from different colonies.

The expected rate of reversal of a single point mutation by error-prone PCR, assuming a mutagenesis rate of 0.7% (10), would be expected to be <1%.

Thus large DNA sequences can be reassembled from a random mixture of small fragments by a reaction that is surprisingly efficient and simple. One application of this technique is the recombination or shuffling of related sequences based on homology. A second application is the assembly of a large product polynucleotide by PCR amplification of component polynucleotides (oligonucleotides) having overlapping regions of homology to form annealed joints during PCR amplification.

Example 2
One-Step Circular Plasmid Assembly From Oligonucleotides

Figure 6:
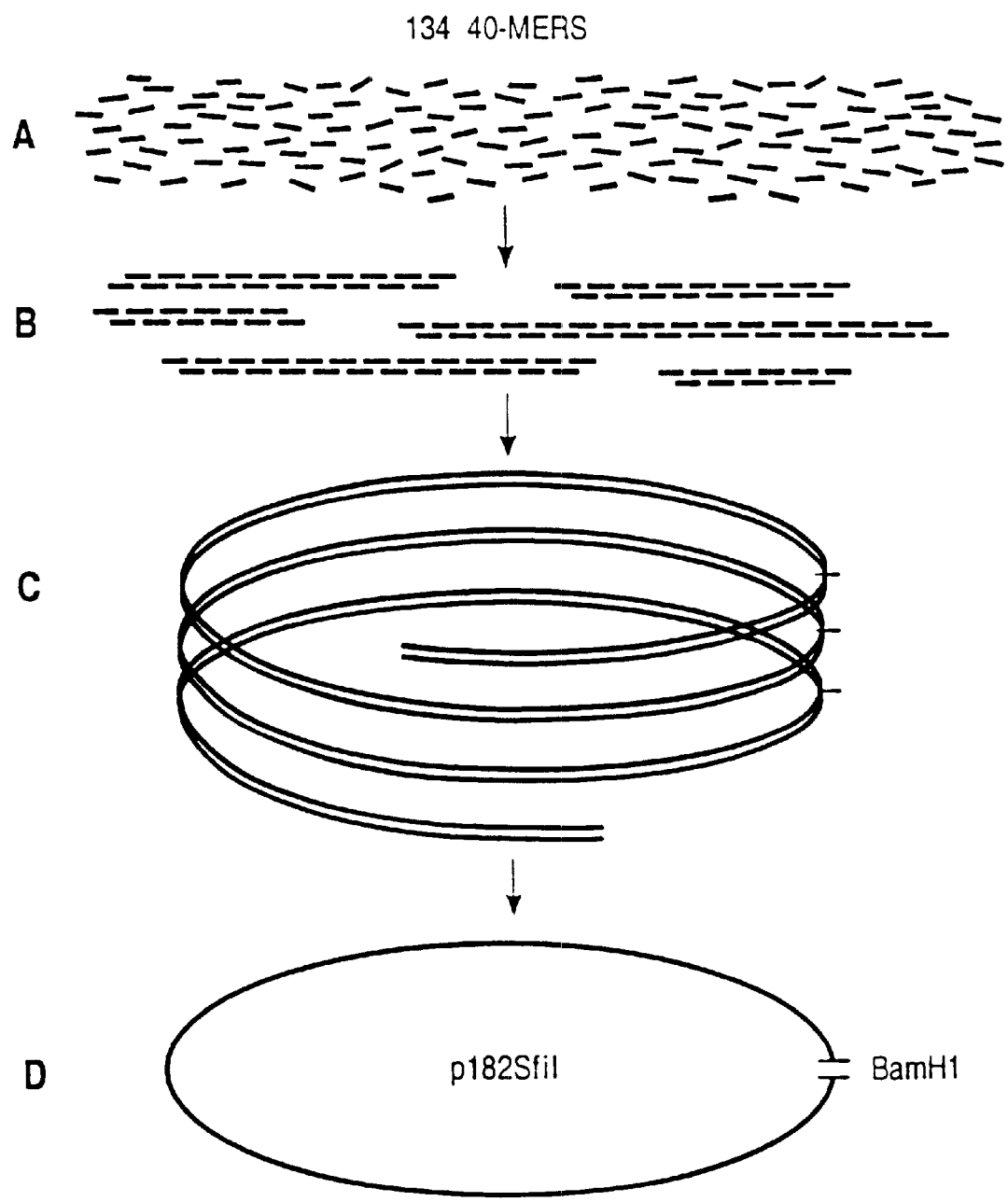
FIG. 6 Schematic of plasmid construction by overlapping fragment PCR as performed in Experimental Examples.

This example demonstrates assembly of a 2.71 kb plasmid p182SfiI (Stemmer (1994) *Nature* 370: 389) which encodes the gene and promoter region for R-TEM1 β-lactamase. A collection of 132 component oligonucleotides, each 40 bases in length, as well as one 56-mer and one 47-mer (see, FIGS. 5A–E) were synthesized and used to assemble the plasmid by end-complementary polymerase reaction (ECPR) employing the overlapping ends of the oligonucleotides. This collection of component polynucleotides collectively encode the plasmid p182SfiI. The plus strand and the minus strand were each initially directed by oligonucleotides 40 nucleotides long which, upon assembly, overlapped by 20 nucleotides (FIG. 6). The oligonucleotides were synthesized and 5'-phosphorylated simultaneously on a 96-well parallel-array DNA synthesizer using standard phosphoramidite chemistry. After cleavage from the solid support and deprotection, the dried down oligonucleotides were resuspended in distilled water and used without further purification.

Figure 7:
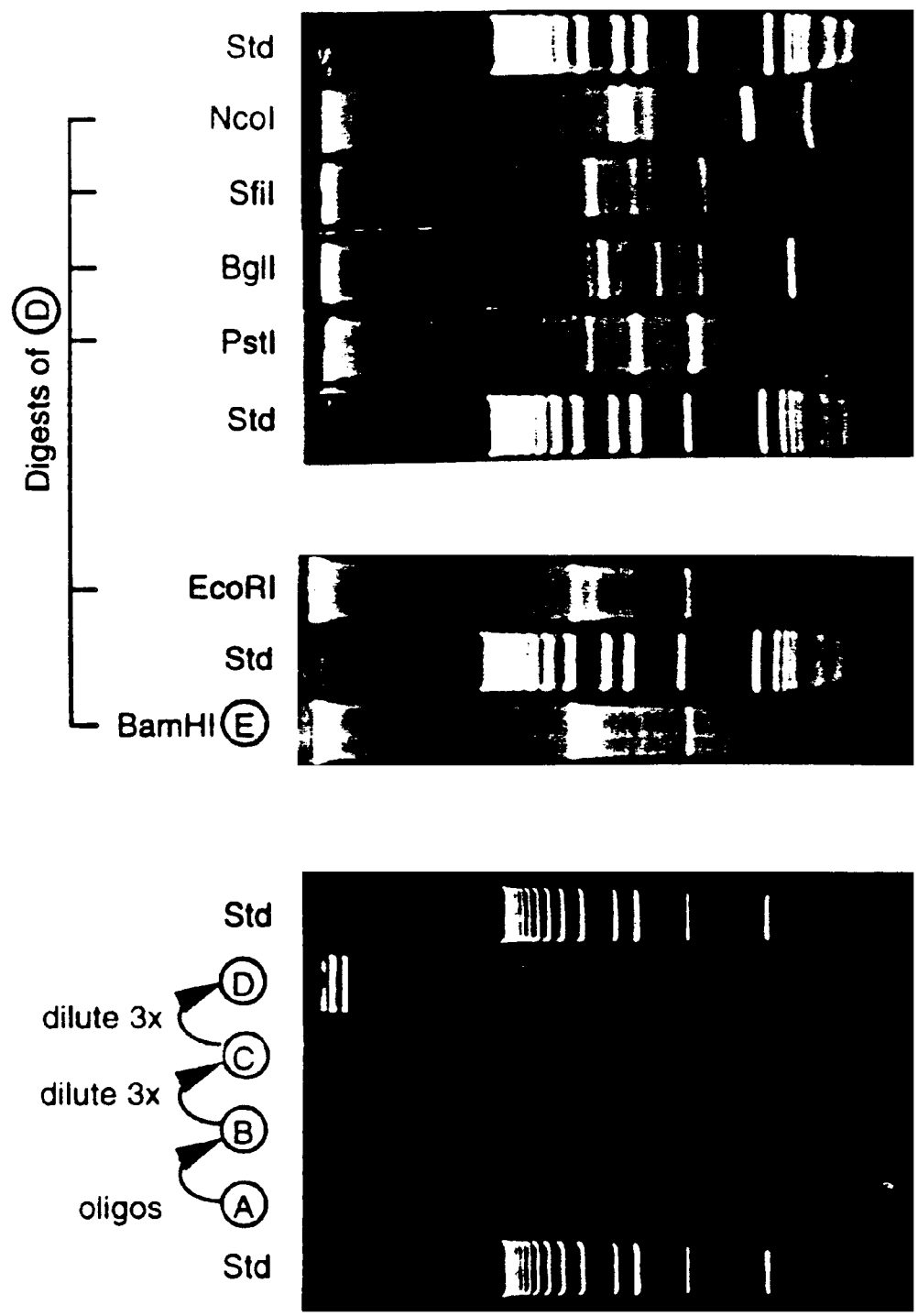
FIG. 7 Agarose gel electrophoresis of products generated during construction of the 2.7 kb circular plasmid p182SfiI by end-complementary polymerase reaction. The circled letters refer to aliquots removed from various amplification reactions: (A) is the mixture of oligonucleotides without polymerase, (B) is the product of the first set of amplification cycles, (C) is the product of the second set of amplification cycles, (D) is the final product.

The oligonucleotides were diluted to a final concentration (all oligos combined) of 1 $\mu$M (14 ng/$\mu$l) in 20 $\mu$l of GeneAMP XL PCR Mix (Perkin-Elmer, Branchburg, N.J.; 0.2 mM each dNTP, 2.2 mM $MgCl_2$, 50 mM KCl, 10 mM Tris-HCl pH 9.0, 0.1% Triton X-100). An aliquot of the reaction mix (A) was electrophoresed on an agarose gel (FIG. 7). The reaction was started with 5 $\mu$l of a 50:1 (v/v) mixture of Taq polymerase (Promega, Madison, Wis.) and Pfu polymerase (Stratagene, La. Jolla, Calif.) such that 1 unit of Taq and 0.02 unit of Pfu polymerase were added. The PCR program consisted of the following program: 40° C. for 2 minutes, 72° C. for 10 seconds, then 40 cycles of (94° C. for 15 seconds, 40° C. for 30 seconds, and 72° C. for [10 seconds+1 second/cycle]). An aliquot of the resulting reaction product (B) was electrophoresed on an agarose gel (FIG. 7), the remainder was then diluted 3× with XL PCR Mix and enzyme and amplified with the following program: 25 cycles of (94° C. for 15 seconds, 40° C. for 30 seconds, and 72° C. for [45 seconds +1 second/cycle]). An aliquot of the resulting reaction product (C) was electrophoresed on an agarose gel (FIG. 7) and the remainder then diluted 3× with XL PCR Mix and enzyme and amplified with the following program: 20 cycles of (94° C. for 15 seconds, 40° C. for 30 seconds, and 72° C. for [70 seconds+1 second/cycle]). An aliquot of the resulting reaction product (D) was electrophoresed on an agarose gel (FIG. 7).

The an aliquot of the reaction product (D) was electrophoresed on an agarose gel, as was an aliquot which was digested with BamHI, which verified assembly of large DNA molecules consistent with formation of large concatemers which was resolved to unit length with BamHI digestion. The PCR product obtained by this method was shown to be concatemeric, and was resolvable by BamHI digestion into a single 2.7 kb band by agarose gel electrophoresis.

Aliquots of reaction product (D) were digested with various restriction enzymes (shown in FIG. 7). FIG. 7 shows that the unique cutters EcoRI and BamHI liberated a 2.71 kb fragment consistent with the size of a complete 2.71 kb plasmid p182SfiI (Stemmer (1994) *Nature* 370: 389, incorporated herein by reference). Furthermore, the digestion results with NcoI, SfiI, PstI, and BglII all yielded fragments consistent with the restriction map of the complete 2.71 kb plasmid p182SfiI.

After digestion of the PCR product with BamHI, the 2.7 kb fragment was gel purified and ligated with ligase, and transformed into *E. coli*.and transformed into *E. coli* K-12. Tetracycline-resistant transformants were selected.

This example demonstrates that the circular DNA assembly method allows for rapid and inexpensive construction of long DNA sequences, such as genes, gene libraries, plasmids, viral genomes, etc. The assembly method facilitates several mutagenesis approaches, such as point mutagenesis, combinatorial cassette mutagenesis, and doping, or mixing in other nucleotides during oligonucleotide synthesis. Deliberate modifications to the DNA sequence can be made simply by substituting one or more new oligos followed by reassembly. To reduce the rate of PCR mutagenesis during assembly, the addition of a proofreading polymerase can assure efficient long-read PCR reactions by combining high processivity with proofreading.

Example 3
Antibody Germline Assembly From Oligos With Rolling Circle Concatemeric Amplification A scFv antibody with germline sequences ($VH_H251$ and $V_{IA}25$) was constructed from 19 oligonucleotides by cyclized assembly. The oligos were at 2–20 ng per $\mu$l in PCR Mix. the program was 20 cycles of (94° C. for 15s, 48° C. for 30s, 72° C. for 30+1s/cycle). The size of the product of this reaction was 200–500 bp. The PCR product was diluted 4-fold in PCR Mix and PCR was run for 24 cycles of (94° C. for 15s, 55° C. for 30s, 72° C. for 30+8s/cycle), followed by one additional 3-fold dilution and 20 cycles of (94° C. for 15s, 55° C. for 30s, 72° C. for 30+8s/cycle). The product was >50 kilobases, and after digestion with SfiI and NotI resulted in a single DNA fragment of the correct size.

FIG. 8 shows a schematic for end-complementary polymerase reaction (ECPR) in conjunction with parallel-processing PCR to amplify very large polynucleotides, such as those larger than can be amplified reliably by conventional PCR using only a single primer set.

Example 4
Plasmid Assembly With Rolling Circle Concatemeric Amplification pGJ103 is a 5.5 kilobase plasmid containing an intact ars operon (Ji and Silver (1992) *Proc. Natl. Acad. Sci.* (*USA*) 89: 9474).

In one example, pGJ103 was digested with DNAseI into random 100–400 bp fragments which were reassembled by circular shuffling in PCR Mix with a program of 50 cycles of (94° C. for 15s, 68° C. for 30 s+8s/cycle), using three different concentrations of fragments. Each reassembly yielded a product of >50 kb which was digested with BamHI to yield a single band of the correct (predicted) size, which was ligated, transformed into *E. coli*, and preplated on increasing levels of arsenate to select for up-mutants.

Cells and Plasmids

Plasmid pGJ103 is pUC19 derivative containing the 2.5 kb arsenic resistance operon from *S. aureus* plasmid pI258. *E. coli* strain TG1 was obtained commercially (Pharmacia, Tarrytown, N.J.). Sodium arsenate (Sigma) was used as a 2.5 M stock solution, neutralized to pH 7 with NaOH. Selection for increased arsenate resistance was performed at 35° C. on agar plates with LB medium (Life Technologies) containing varying concentrations of arsenate.

The 5.5 kb plasmid pGJ103 was fragmented by sonication into fragments of 400–1500 bp, and reassembled by PCR using Perkin Elmer XL-PCR reagents with 10% PEG-6000, using PCR without added primers. The PCR program for the assembly was 90° C. 30s, than 60 cycles of: 94° C. 20s, 40–45° C. 30s, 72° C., 39s+1s per cycle in a PTC-150 minicycler (M J Research, Watertown, Mass.). The PCR process yielded plasmid multimers of about 15 to 40 kb in size, that were digested into 5.5 kb monomers with the restriction enzyme BamHI, which has a single unique site in plasmid pGJ103. The 5.5 kb plasmid monomer was purified from an agarose gel after electrophoresis, and after self-ligation, it was electroporated into electrocompetent *E. coli* TG1 cells.

Arsenate Resistance Selection

Transformed E. coli cells were plated on LB plates containing a range of concentrations of sodium and arsenate and incubated at 37° C. for 24 hrs., and at least 1,000 colonies from the plates with the highest arsenate levels were pooled by scraping the plates. The harvested cells were grown in liquid in the presence of the same concentration of arsenate as in the petri dish and a plasmid pool was prepared from this liquid culture. Rounds 2–4 were identical to round 1, except that the cells were plated at higher arsenate levels.

Arsenate Resistance Quantification

Induced inoculum cells of E. coli TG1(pGJ103), wild type ars operon, and TG1 with mutant pGJ103 plasmid pools were grown overnight at 37° C. in 2 mM or 50 mM arsenate, respectively. Equal amounts of cells (by turbidity as OD600 nm) were on plates containing a range of concentrations of arsenate and grown for 18 hrs. at 37° C. Cell growth was quantitated by resuspending the cells and measuring the OD600 nm.

Arsenate Detoxification Assay

The ability of E. coli constructs to detoxify arsenate was measured by intact cell arsenate reduction assay using radioactive 73AsO43—as substrate and separation of arsenate and arsenite of by thin layer chromatography, followed by quantitation in an Ambis radioactive counter.

DNA Sequencing

The sequence of the entire operon after selection was determined by dideoxy DNA sequencing using fluorescent terminating substrate and an ABI sequencer.

Results and Discussion

The wild type plasmid pGJ103 ars operon confers on E. coli strain TG1 resistance to up to 4 mM arsenate when grown on LB plates at 37° C. for 24 hrs. Selection round one, which was plated on 2, 4, 8, 16 and 32 mM arsenate, yielded about 2,000 colonies growing at 16 mM arsenate. Selection round two was plated 16, 32, 64 and 128 mM arsenate and yielded about 4,000 colonies growing at 64 mM arsenate. Round three was plated at 64, 128 and 256 mM arsenate and yielded about 1,500 colonies at 128 mM arsenate, and round 4 was plated on 128, 256 and 512 mM arsenate. Colonies were harvested from the plates with 256 mM arsenate and replated on 200, 300 and 400 mM arsenate. Single colonies from plates with 400 mM arsenate were grown in liquid culture with 400 mM arsenate and frozen at −70° C., and used for further characterization. Resistance levels were increased by DNA shuffling to arsenate (as selected) and also to arsenite and antimony salts (FIG. 12), which are the two toxic oxyanions to which resistance requires the ArsB membrane transporter but not the ArsC arsenate reductase enzyme. In this growth experiment, done with the pool from three cycles of DNA shuffling (which retained good growth in LB broth), not only was growth clear about 100 mM AsO43−, but increased resistance to arsenite (AsO2−) and antimony (SbO3+) was clearly=20 shown. These results require mutational effects beyond those possibly limited to the arC gene, which affects resistance to arsenate alone.

Chromosomal Integration

Cells selected and grown at and above 128 mM arsenate resulted in smaller growth, lower cell growth yields, and in low and variable plasmid yields. Plasmids were isolated that had apparently lost the arsenate operon, and most cells showed a complete loss of plasmids. It appeared that the DNA shuffling plus selection for high arsenate resistance resulted in integration of the ars operon into the E. coli chromosome, since the ars operon could be recovered from chromosomal DNA of clones which had lost the entire plasmid by conventional PCR amplification with "upstream" and "downstream" oligonucleotide primers.

Integration Mechanism

The arsenate resistance operon of plasmid pGJ103 is flanked on both sides by 200 bp inverted homologous regions, which appear to be the terminal portions of site-specific recombiziase genes. Attempts to recover the operon from the total cellular DNA of highly resistant cells by PCR showed that oligonucleotide primers near the inside ends of the recombinanse genes, immediately flanking the arsenate genes, yielded a PCR product of the correct size (2.0 kb) and with the expected restriction nuclease site pattern. However, primers located toward the middle or near the outside ends of the 200 bp homologous sequences did not yield predicted PCR products with the intact ars operon. Presumably, chromosomal integration was selected because the integrated operon somehow resulted in increased arsenate resistance and the homologous sequences at the ends of the ars operon facilitated chromosomal integration by recombination.

Chromosomal Ars Operon

The chromosome of E. coli normally contains an arsenate resistance operon which is distantly related to the pI258 operon and results in a low level of arsenate resistance. The operon which was recovered from the chromosome of highly resistant cells by PVR was shown by restriction mapping and by DNA sequencing to be derived from the pI258 operon, and not from the E. coli K-12 chromosomal operon.

Chromosomal Shuffling

Because the cells recovered from 128 mM arsenate did not contain plasmid DNA, the shuffling for round 4 was performed on the PCR product which was obtained from the chromosomal DNA of the cells selected in round 3. This PCR product was combined with a 10-fold lower molar amount of the plasmid DNA obtained from round 2 cells, and the mixture was fragmented, shuffled and selected as for earlier rounds.

Cloning and Characterization of the Integrated Operon

The conventional PCR product which was obtained from the chromosomal DNA of cells grown at 400 mM arsenate was cloned into the polylinker site of pUC19. This construct was similar to pGJ103 except that it lacked the 200 bp inverted homologous DNA flanking the arsenate operon. Cells containing this plasmid were resistant only up to about 10 mM arsenate. The reason for this loss of arsenate resistance level is not known. The DNA sequence of this cloned chromosomal operon showed thirteen base changes relative to the original sequence. The arsR gene contained two silent mutations (T389C and T429C. The arsB gene contained ten base changes, and one base change occurred in the non-coding area past the end of the arsC gene (G2469C). Of the ten base changes in arsB, three resulted in amino acid alterations: base T1281C change resulted in amino acid change L232S, base T1317C change resulted in amino acid change F244S, and base T1853C change resulted in amino acid change Y423H, all three involving a change toward a more hydrophilic residue via a T to C transition. The seven silent mutations were T961G, A976G, T1267C, A1402G, T1730C, T1819C and T1844C.

Arsenate Reductase Activity

The activity of arsenate reductase by whole mutant cells after the third cycle was increased about 50-fold (FIG. 13) to the wild type initial strain with plasmid pGJ103. This increase in whole cell reductase rate appeared to be more dependent on an increase in rate reduction and not on an enhanced affinity of arsenate for the cells (data not shown). This is consistent with the finding that the mutations occurred in the efflux transport protein and not in the arsenate reductase itself.

Although the present invention has been described in some detail by way of illustration for purposes of clarity of understanding, it will be apparent that certain changes and modifications may be practiced within the scope of the claims.

What is claimed is:

1. A method of multiplex amplification, comprising
contacting at least first and second noncontiguous polynucleotide sequences with at least first, second, third and fourth bivalent primers under amplification conditions,
wherein the 3' end of the first bivalent primer is complementary to the 3' end of the first polynucleotide sequence, and to the 5' end of the second bivalent primer,
the 3' end of the second bivalent primer is complementary to the 3' end of the second polynucleotide sequence and to the 5' end of the first bivalent primer,
the 3' end of the third bivalent primer is complementary to the 3' end of the complement of the first polynucleotide sequence, and to the 5' end of the fourth bivalent primer;
the 3' end of the fourth bivalent primer is complementary to the 3' end of the complement of the second polynucleotide sequence, and to the 5' end of the third bivalent primer;
the first, and second bivalent primers do not form stable hybrids with each other due to lack of sequence identity in internal segments of the first and second bivalent primers;
the third and fourth bivalent primers do not form stable hybrids with each other due to lack of sequence identity in internal segments of the third and fourth bivalent primers;
conducting a multi-cyclic amplification reaction to form a contiguous amplification product comprising equimolar amounts of the first and second polynucleotide sequences and an internal segment from one of the bivalent primers.

2. The method of claim 1, wherein the first and second noncontiguous polynucleotides sequences are exons of the same gene.

3. The method of claim 1, further comprising digesting the amplification product with a restriction enzyme having a site in the internal segment of the amplification product to separate the first and second polynucleotide sequences.

4. The method of claim 1, wherein at least one of the bivalent primers further comprises a transcriptional promoter.

5. A method of multiplex amplification, comprising
contacting at least first and second noncontiguous polynucleotide sequences with at least first and second bivalent primers and first and second flanking primers under amplification conditions,
wherein the 3' end of the first bivalent primer is complementary to the 3' end of the first polynucleotide sequence, and to the 5' end of the second polynucleotide,
the 3' end of the second bivalent primer is complementary to the 3' end of the second polynucleotide sequence and to the 5' end of the first polynucleotide,
the first flanking primer is complementary to the 3' end of the complement of the first polynucleotide;
the second flanking primer is complementary to the 3' end of the complement of the second polynucleotide
the first, and second bivalent primers do not form stable hybrids with each other due to lack of sequence identity in internal segments of the first and second bivalent primers;

conducting a multi-cyclic amplification reaction to form a contiguous amplification product comprising equimolar amounts of the first and second polynucleotide sequences and an internal segment from one of the bivalent primers.

6. The method of claim 5 wherein the first and second noncontiguous polynucleotides sequences are exons of the same gene.

7. The method of claim 5, further comprising digesting the amplification product with a restriction enzyme having a site in the internal segment of the amplification product to separate the first and second polynucleotide sequences.

8. The method of claim 5, wherein at least one of the bivalent primers further comprises a transcriptional promoter.

* * * * *